United States Patent
Julian et al.

(10) Patent No.: US 12,076,102 B2
(45) Date of Patent: Sep. 3, 2024

(54) CONNECTOR DEVICE FOR A CONTROLLABLE INSTRUMENT

(71) Applicant: INTUITIVE SURGICAL OPERATIONS, INC., Sunnyvale, CA (US)

(72) Inventors: Christopher A. Julian, Los Gatos, CA (US); Amir Belson, Los Altos, CA (US); Aaron W. Brown, San Jose, CA (US); Mark Harasym, San Jose, CA (US); Marc S. Kreidler, Sunnyvale, CA (US); Robert M. Ohline, Redwood City, CA (US); Scott J. Reiner, San Jose, CA (US); Enrique Romo, Fresno, CA (US); Charles E. Swinehart, San Jose, CA (US); Katherine Whitin, Redwood City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 1057 days.

(21) Appl. No.: 16/928,173

(22) Filed: Jul. 14, 2020

(65) Prior Publication Data
US 2021/0030260 A1   Feb. 4, 2021

Related U.S. Application Data

(63) Continuation of application No. 16/123,309, filed on Sep. 6, 2018, now Pat. No. 10,736,490, which is a
(Continued)

(51) Int. Cl.
*A61B 34/00* (2016.01)
*A61B 1/00* (2006.01)
(Continued)

(52) U.S. Cl.
CPC .......... *A61B 34/71* (2016.02); *A61B 1/00128* (2013.01); *A61B 1/0016* (2013.01);
(Continued)

(58) Field of Classification Search
CPC ... A61B 1/0053; A61B 34/71; A61B 1/00128; A61B 1/0055; A61B 1/0057; A61B 2017/00477
See application file for complete search history.

(56) References Cited

U.S. PATENT DOCUMENTS 616,672 A    12/1898  Kelling
1,590,919 A   6/1926  Wahl et al.
(Continued)

FOREIGN PATENT DOCUMENTS

DE    2823025 C2   2/1986
DE    3707787 A1   9/1988
(Continued)

OTHER PUBLICATIONS

"Active endoscope (ELASTOR, shape memory alloy robot)," 9 pages including 3 figures and 4 photographs. Accessed Feb. 21, 2002. Internet: http://mozu.mes.titech.ac.jp/research/medical/endoscope/endoscope.html.
(Continued)

*Primary Examiner* — John P Leubecker
*Assistant Examiner* — Jae Woo
(74) *Attorney, Agent, or Firm* — JONES ROBB, PLLC

(57) ABSTRACT

A medical instrument may comprise a first articulatable segment having a first diameter, and a second articulatable segment having a second diameter smaller than the first diameter, wherein the second articulatable segment is coupled to the first articulatable segment and extends in a distal direction past the first articulatable segment. The instrument may also comprise a first force transmission
(Continued)

element coupled to the first articulatable segment and extending in a proximal direction from the first articulatable segment to a first connector portion, the first connector portion being configured to be releasably coupled with a first actuator, and a second force transmission element coupled to the second articulatable segment and extending in a proximal direction from the second articulatable segment to a second connector portion, the second connector portion being configured to be releasably coupled with a second actuator. The first and second force transmission elements may be configured to transmit actuation forces, respectively, to articulate the first and second articulatable segments independently of one another.

20 Claims, 22 Drawing Sheets

Related U.S. Application Data continuation of application No. 14/537,127, filed on Nov. 10, 2014, now Pat. No. 10,105,036, which is a continuation of application No. 10/988,212, filed on Nov. 12, 2004, now Pat. No. 8,888,688.

(51) Int. Cl.
  *A61B 1/005* (2006.01)
  *A61B 1/008* (2006.01)
  *A61B 1/31* (2006.01)
  *A61B 17/00* (2006.01)

(52) U.S. Cl.
  CPC .......... *A61B 1/0053* (2013.01); *A61B 1/0055* (2013.01); *A61B 1/0057* (2013.01); *A61B 1/008* (2013.01); *A61B 1/31* (2013.01); *A61B 2017/003* (2013.01); *A61B 2017/00477* (2013.01)

(56) References Cited

U.S. PATENT DOCUMENTS

| | | |
|---|---|---|
| 2,241,576 A | 5/1941 | Charles |
| 2,510,198 A | 6/1950 | Tesmer |
| 2,533,494 A | 12/1950 | Mitchell, Jr. |
| 2,767,705 A | 10/1956 | Moore |
| 3,060,972 A | 10/1962 | Sheldon |
| 3,071,161 A | 1/1963 | Ulrich |
| 3,096,962 A | 7/1963 | Meijs |
| 3,162,214 A | 12/1964 | Wilfred, Jr. |
| 3,168,274 A | 2/1965 | Street |
| 3,190,286 A | 6/1965 | Stokes |
| 3,266,059 A | 8/1966 | Stelle |
| 3,430,662 A | 3/1969 | Guarnaschelli |
| 3,497,083 A | 2/1970 | Victor et al. |
| 3,546,961 A | 12/1970 | Marton |
| 3,610,231 A | 10/1971 | Takahashi et al. |
| 3,625,084 A | 12/1971 | Siebert |
| 3,643,653 A | 2/1972 | Takahashi et al. |
| 3,739,770 A | 6/1973 | Mori |
| 3,773,034 A | 11/1973 | Burns et al. |
| 3,780,740 A | 12/1973 | Rhea |
| 3,858,578 A | 1/1975 | Milo |
| 3,871,358 A | 3/1975 | Fukuda et al. |
| 3,897,775 A | 8/1975 | Furihata |
| 3,913,565 A | 10/1975 | Kawahara |
| 3,946,727 A | 3/1976 | Okada et al. |
| 3,990,434 A | 11/1976 | Free |
| 4,054,128 A | 10/1977 | Seufert et al. |
| 4,176,662 A | 12/1979 | Frazer |
| 4,233,981 A | 11/1980 | Schomacher |
| 4,236,509 A | 12/1980 | Takahashi et al. |
| 4,240,435 A | 12/1980 | Yazawa et al. |
| 4,272,873 A | 6/1981 | Dietrich |
| 4,273,111 A | 6/1981 | Tsukaya |
| 4,286,585 A | 9/1981 | Ogawa |
| 4,327,711 A | 5/1982 | Takagi |
| 4,366,810 A | 1/1983 | Slanetz, Jr. |
| 4,393,728 A | 7/1983 | Larson et al. |
| 4,418,688 A | 12/1983 | Loeb |
| 4,432,349 A | 2/1984 | Oshiro |
| 4,483,326 A | 11/1984 | Yamaka et al. |
| 4,489,826 A | 12/1984 | Dubson |
| 4,494,417 A | 1/1985 | Larson et al. |
| 4,499,895 A | 2/1985 | Takayama |
| 4,503,842 A | 3/1985 | Takayama |
| 4,517,652 A | 5/1985 | Bennett et al. |
| 4,534,339 A | 8/1985 | Collins et al. |
| 4,543,090 A | 9/1985 | McCoy |
| 4,551,061 A | 11/1985 | Olenick |
| 4,559,928 A | 12/1985 | Takayama |
| 4,566,843 A | 1/1986 | Iwatsuka et al. |
| 4,577,621 A | 3/1986 | Patel |
| 4,592,341 A | 6/1986 | Omagari et al. |
| 4,601,283 A | 7/1986 | Chikama |
| 4,601,705 A | 7/1986 | McCoy |
| 4,601,713 A | 7/1986 | Fuqua |
| 4,621,618 A | 11/1986 | Omagari |
| 4,624,243 A | 11/1986 | Lowery et al. |
| 4,630,649 A | 12/1986 | Oku |
| 4,643,184 A | 2/1987 | Mobin-Uddin |
| 4,646,722 A | 3/1987 | Silverstein et al. |
| 4,648,733 A | 3/1987 | Merkt |
| 4,651,718 A | 3/1987 | Collins et al. |
| 4,655,257 A | 4/1987 | Iwashita |
| 4,683,773 A | 8/1987 | Diamond |
| 4,686,963 A | 8/1987 | Cohen et al. |
| 4,696,544 A | 9/1987 | Costella |
| 4,712,969 A | 12/1987 | Kimura |
| 4,726,355 A | 2/1988 | Okada |
| 4,753,222 A | 6/1988 | Morishita |
| 4,753,223 A | 6/1988 | Bremer |
| 4,754,909 A | 7/1988 | Barker et al. |
| 4,784,117 A | 11/1988 | Miyazaki |
| 4,787,369 A | 11/1988 | Allred, III et al. |
| 4,788,967 A | 12/1988 | Ueda |
| 4,790,624 A | 12/1988 | Van Hoye et al. |
| 4,793,326 A | 12/1988 | Shishido |
| 4,796,607 A | 1/1989 | Allred, III et al. |
| 4,799,474 A | 1/1989 | Ueda |
| 4,800,890 A | 1/1989 | Cramer |
| 4,807,593 A | 2/1989 | Ito |
| 4,815,450 A | 3/1989 | Patel |
| 4,832,473 A | 5/1989 | Ueda |
| 4,834,068 A | 5/1989 | Gottesman |
| 4,846,573 A | 7/1989 | Taylor et al. |
| 4,873,965 A | 10/1989 | Danieli |
| 4,873,990 A | 10/1989 | Holmes et al. |
| 4,879,991 A | 11/1989 | Ogiu |
| 4,884,557 A | 12/1989 | Takehana et al. |
| 4,890,602 A | 1/1990 | Hake |
| 4,895,431 A | 1/1990 | Tsujiuchi et al. |
| 4,899,731 A | 2/1990 | Takayama et al. |
| 4,904,048 A | 2/1990 | Sogawa et al. |
| 4,917,114 A | 4/1990 | Green et al. |
| 4,919,112 A | 4/1990 | Siegmund |
| 4,930,494 A | 6/1990 | Takehana et al. |
| 4,949,927 A | 8/1990 | Madocks et al. |
| 4,957,486 A | 9/1990 | Davis |
| 4,969,709 A | 11/1990 | Sogawa et al. |
| 4,971,035 A | 11/1990 | Ito |
| 4,977,886 A | 12/1990 | Takehana et al. |
| 4,977,887 A | 12/1990 | Gouda |
| 4,987,314 A | 1/1991 | Gotanda et al. |
| 5,005,558 A | 4/1991 | Aomori |
| 5,005,559 A | 4/1991 | Blanco et al. |
| 5,014,709 A | 5/1991 | Bjelkhagen et al. |
| 5,018,509 A | 5/1991 | Suzuki et al. |
| 5,025,778 A | 6/1991 | Silverstein et al. |
| 5,025,804 A | 6/1991 | Kondo |
| 5,050,585 A | 9/1991 | Takahashi |
| 5,059,158 A | 10/1991 | Bellio et al. |

(56) References Cited

U.S. PATENT DOCUMENTS

| | | | |
|---|---|---|---|
| 5,060,632 A | 10/1991 | Hibino et al. | |
| 5,083,549 A | 1/1992 | Cho et al. | |
| 5,090,956 A | 2/1992 | McCoy | |
| 5,092,901 A | 3/1992 | Hunter et al. | |
| 5,103,403 A | 4/1992 | Chhayder et al. | |
| 5,125,395 A | 6/1992 | Adair | |
| 5,127,393 A | 7/1992 | McFarlin et al. | |
| 5,158,086 A * | 10/1992 | Brown | A61B 1/0057 |
| | | | 600/152 |
| 5,159,446 A | 10/1992 | Hibino et al. | |
| 5,166,787 A | 11/1992 | Irion | |
| 5,174,276 A | 12/1992 | Crockard | |
| 5,174,277 A | 12/1992 | Matsumaru | |
| 5,179,935 A | 1/1993 | Miyagi | |
| 5,184,601 A * | 2/1993 | Putman | A61B 34/30 |
| | | | 901/17 |
| 5,188,111 A | 2/1993 | Yates et al. | |
| 5,203,319 A | 4/1993 | Danna et al. | |
| 5,207,695 A | 5/1993 | Trout, III | |
| 5,217,001 A | 6/1993 | Nakao et al. | |
| 5,218,280 A | 6/1993 | Edwards | |
| 5,220,911 A | 6/1993 | Tamura | |
| 5,228,429 A | 7/1993 | Hatano | |
| 5,234,448 A | 8/1993 | Wholey et al. | |
| 5,239,982 A | 8/1993 | Trauthen | |
| 5,243,967 A | 9/1993 | Hibino | |
| 5,250,058 A | 10/1993 | Miller et al. | |
| 5,250,167 A | 10/1993 | Adolf et al. | |
| 5,251,611 A | 10/1993 | Zehel et al. | |
| 5,253,647 A | 10/1993 | Takahashi et al. | |
| 5,254,809 A | 10/1993 | Martin | |
| 5,257,617 A | 11/1993 | Takahashi | |
| 5,259,364 A | 11/1993 | Bob et al. | |
| 5,268,082 A | 12/1993 | Oguro et al. | |
| 5,269,289 A | 12/1993 | Takehana et al. | |
| 5,271,381 A | 12/1993 | Ailinger et al. | |
| 5,271,382 A | 12/1993 | Chikama | |
| 5,279,610 A | 1/1994 | Park et al. | |
| 5,297,443 A | 3/1994 | Wentz | |
| 5,299,143 A | 3/1994 | Hellinga et al. | |
| 5,324,284 A | 6/1994 | Imran | |
| 5,325,845 A | 7/1994 | Adair | |
| 5,337,732 A | 8/1994 | Grundfest et al. | |
| 5,337,733 A | 8/1994 | Bauerfeind et al. | |
| 5,343,874 A | 9/1994 | Picha et al. | |
| 5,347,987 A | 9/1994 | Feldstein et al. | |
| 5,348,259 A | 9/1994 | Blanco et al. | |
| 5,368,015 A | 11/1994 | Wilk | |
| 5,370,108 A | 12/1994 | Miura et al. | |
| 5,377,678 A | 1/1995 | Dumoulin et al. | |
| 5,383,467 A | 1/1995 | Auer et al. | |
| 5,383,852 A | 1/1995 | Stevens-Wright | |
| 5,389,222 A | 2/1995 | Shahinpoor | |
| 5,394,864 A | 3/1995 | Kobayashi et al. | |
| 5,396,879 A | 3/1995 | Wilk et al. | |
| 5,400,769 A | 3/1995 | Tanii et al. | |
| 5,402,768 A | 4/1995 | Adair | |
| 5,411,508 A | 5/1995 | Bessler et al. | |
| 5,413,108 A | 5/1995 | Alfano | |
| 5,421,337 A | 6/1995 | Richards-Kortum et al. | |
| 5,421,338 A | 6/1995 | Crowley et al. | |
| 5,425,738 A | 6/1995 | Gustafson et al. | |
| 5,429,118 A | 7/1995 | Cole et al. | |
| 5,431,645 A | 7/1995 | Smith et al. | |
| 5,439,000 A | 8/1995 | Gunderson et al. | |
| 5,451,221 A | 9/1995 | Cho et al. | |
| 5,456,714 A | 10/1995 | Owen | |
| 5,460,166 A | 10/1995 | Yabe et al. | |
| 5,460,168 A | 10/1995 | Masubuchi et al. | |
| 5,469,840 A | 11/1995 | Tanii et al. | |
| 5,479,930 A | 1/1996 | Gruner et al. | |
| 5,482,029 A | 1/1996 | Sekiguchi et al. | |
| 5,486,182 A | 1/1996 | Nakao et al. | |
| 5,487,385 A | 1/1996 | Avitall | |
| 5,487,757 A | 1/1996 | Truckai et al. | |
| 5,489,256 A | 2/1996 | Adair | |
| 5,492,131 A | 2/1996 | Galel | |
| 5,503,616 A | 4/1996 | Jones | |
| 5,507,287 A | 4/1996 | Palcic et al. | |
| 5,507,717 A | 4/1996 | Kura et al. | |
| 5,522,788 A | 6/1996 | Kuzmak | |
| 5,531,664 A | 7/1996 | Adachi et al. | |
| 5,535,759 A | 7/1996 | Wilk | |
| 5,551,945 A | 9/1996 | Yabe et al. | |
| 5,556,370 A | 9/1996 | Maynard | |
| 5,556,700 A | 9/1996 | Kaneto et al. | |
| 5,558,619 A | 9/1996 | Kami et al. | |
| 5,558,665 A | 9/1996 | Kieturakis | |
| 5,577,992 A | 11/1996 | Chiba et al. | |
| 5,586,968 A | 12/1996 | Grundl et al. | |
| 5,590,660 A | 1/1997 | MacAulay et al. | |
| 5,601,087 A | 2/1997 | Gunderson et al. | |
| 5,602,449 A | 2/1997 | Krause et al. | |
| 5,620,408 A | 4/1997 | Vennes et al. | |
| 5,624,380 A | 4/1997 | Takayama et al. | |
| 5,624,381 A | 4/1997 | Kieturakis | |
| 5,626,553 A | 5/1997 | Frassica et al. | |
| 5,631,040 A | 5/1997 | Takuchi et al. | |
| 5,645,064 A | 7/1997 | Littmann et al. | |
| 5,645,520 A | 7/1997 | Nakamura et al. | |
| 5,647,368 A | 7/1997 | Zeng et al. | |
| 5,647,840 A | 7/1997 | Damelio et al. | |
| 5,651,366 A | 7/1997 | Liang et al. | |
| 5,651,769 A | 7/1997 | Waxman et al. | |
| 5,653,690 A | 8/1997 | Booth et al. | |
| 5,658,238 A | 8/1997 | Suzuki et al. | |
| 5,662,585 A | 9/1997 | Willis et al. | |
| 5,662,587 A | 9/1997 | Grundfest et al. | |
| 5,662,621 A | 9/1997 | Lafontaine | |
| 5,665,050 A | 9/1997 | Benecke | |
| 5,667,476 A | 9/1997 | Frassica et al. | |
| 5,679,216 A | 10/1997 | Takayama et al. | |
| 5,681,260 A | 10/1997 | Ueda et al. | |
| 5,704,898 A * | 1/1998 | Kokish | A61B 34/71 |
| | | | 600/152 |
| 5,720,718 A | 2/1998 | Rosen et al. | |
| 5,725,475 A | 3/1998 | Yasui et al. | |
| 5,728,044 A | 3/1998 | Shan | |
| 5,733,245 A | 3/1998 | Kawano | |
| 5,746,694 A | 5/1998 | Wilk et al. | |
| 5,749,828 A | 5/1998 | Solomon et al. | |
| 5,752,912 A | 5/1998 | Takahashi et al. | |
| 5,759,151 A | 6/1998 | Sturges | |
| 5,762,613 A | 6/1998 | Sutton et al. | |
| 5,765,561 A | 6/1998 | Chen et al. | |
| 5,769,792 A | 6/1998 | Palcic et al. | |
| 5,771,902 A | 6/1998 | Lee et al. | |
| 5,772,597 A | 6/1998 | Goldberger et al. | |
| 5,773,835 A | 6/1998 | Sinofsky | |
| 5,779,624 A | 7/1998 | Chang | |
| 5,807,241 A | 9/1998 | Heimberger | |
| 5,810,715 A | 9/1998 | Moriyama | |
| 5,810,716 A | 9/1998 | Mukherjee et al. | |
| 5,810,717 A | 9/1998 | Maeda et al. | |
| 5,810,776 A | 9/1998 | Bacich et al. | |
| 5,813,976 A | 9/1998 | Filipi et al. | |
| 5,819,749 A | 10/1998 | Lee et al. | |
| 5,827,190 A | 10/1998 | Palcic et al. | |
| 5,827,265 A | 10/1998 | Glinsky et al. | |
| 5,842,973 A | 12/1998 | Bullard | |
| 5,848,972 A | 12/1998 | Triedman et al. | |
| 5,855,565 A | 1/1999 | Bar-Cohen et al. | |
| 5,857,962 A | 1/1999 | Bracci et al. | |
| 5,860,581 A | 1/1999 | Robertson et al. | |
| 5,860,914 A | 1/1999 | Chiba et al. | |
| 5,868,760 A | 2/1999 | McGuckin, Jr. | |
| 5,873,817 A | 2/1999 | Kokish et al. | |
| 5,876,329 A | 3/1999 | Harhen | |
| 5,876,373 A | 3/1999 | Giba et al. | |
| 5,885,208 A | 3/1999 | Moriyama | |
| 5,893,369 A | 4/1999 | Lemole | |
| 5,897,417 A | 4/1999 | Grey | |
| 5,897,488 A | 4/1999 | Ueda | |
| 5,902,254 A | 5/1999 | Magram | |

(56) References Cited

U.S. PATENT DOCUMENTS

| | | |
|---|---|---|
| 5,906,591 A | 5/1999 | Dario et al. |
| 5,908,381 A | 6/1999 | Aznoian et al. |
| 5,911,715 A | 6/1999 | Berg et al. |
| 5,916,146 A | 6/1999 | Allotta et al. |
| 5,916,147 A | 6/1999 | Boury |
| 5,921,915 A | 7/1999 | Aznoian et al. |
| 5,928,136 A | 7/1999 | Barry |
| 5,941,815 A | 8/1999 | Chang |
| 5,941,908 A | 8/1999 | Goldsteen et al. |
| 5,957,833 A | 9/1999 | Shan |
| 5,957,969 A | 9/1999 | Warner et al. |
| 5,968,052 A | 10/1999 | Sullivan, III |
| 5,971,767 A | 10/1999 | Kaufman et al. |
| 5,976,074 A | 11/1999 | Moriyama |
| 5,989,182 A | 11/1999 | Hori et al. |
| 5,989,230 A | 11/1999 | Frassica |
| 5,993,381 A | 11/1999 | Ito |
| 5,993,447 A | 11/1999 | Blewett et al. |
| 5,993,462 A | 11/1999 | Pomeranz et al. |
| 5,996,346 A | 12/1999 | Maynard |
| 6,016,440 A | 1/2000 | Simon et al. |
| 6,033,359 A | 3/2000 | Doi |
| 6,036,636 A | 3/2000 | Motoki et al. |
| 6,036,702 A | 3/2000 | Bachinski et al. |
| 6,042,155 A | 3/2000 | Lockwood |
| 6,048,307 A | 4/2000 | Grundl et al. |
| 6,059,718 A | 5/2000 | Taniguchi et al. |
| 6,063,022 A | 5/2000 | Ben-Haim |
| 6,066,102 A | 5/2000 | Townsend et al. |
| 6,066,132 A | 5/2000 | Chen et al. |
| 6,068,629 A | 5/2000 | Haissaguerre et al. |
| 6,068,638 A | 5/2000 | Makower |
| 6,071,234 A | 6/2000 | Takada |
| 6,096,023 A | 8/2000 | Lemelson |
| 6,096,289 A | 8/2000 | Goldenberg |
| 6,099,464 A | 8/2000 | Shimizu et al. |
| 6,099,465 A | 8/2000 | Inoue |
| 6,099,485 A | 8/2000 | Patterson |
| 6,099,524 A | 8/2000 | Lipson et al. |
| 6,106,510 A | 8/2000 | Lunn et al. |
| 6,109,852 A | 8/2000 | Shahinpoor et al. |
| 6,117,296 A | 9/2000 | Thomson |
| 6,119,913 A | 9/2000 | Adams et al. |
| 6,129,667 A | 10/2000 | Dumoulin et al. |
| 6,129,683 A | 10/2000 | Sutton et al. |
| 6,141,577 A | 10/2000 | Rolland et al. |
| 6,149,581 A | 11/2000 | Klingenstein |
| 6,162,171 A | 12/2000 | Ng et al. |
| 6,174,280 B1 | 1/2001 | Oneda et al. |
| 6,174,291 B1 | 1/2001 | McMahon et al. |
| 6,178,346 B1 | 1/2001 | Amundson et al. |
| 6,179,776 B1 | 1/2001 | Adams et al. |
| 6,185,448 B1 | 2/2001 | Borovsky |
| 6,201,989 B1 | 3/2001 | Whitehead et al. |
| 6,203,493 B1 | 3/2001 | Ben-Haim |
| 6,203,494 B1 | 3/2001 | Moriyama |
| 6,210,337 B1 | 4/2001 | Dunham et al. |
| 6,221,006 B1 | 4/2001 | Dubrul et al. |
| 6,226,547 B1 | 5/2001 | Lockhart et al. |
| 6,233,476 B1 | 5/2001 | Strommer et al. |
| 6,241,657 B1 | 6/2001 | Chen et al. |
| 6,249,076 B1 | 6/2001 | Madden et al. |
| 6,264,086 B1 | 7/2001 | McGuckin, Jr. |
| 6,270,453 B1 | 8/2001 | Sakai |
| 6,293,907 B1 | 9/2001 | Axon et al. |
| 6,306,081 B1 | 10/2001 | Ishikawa et al. |
| 6,309,346 B1 | 10/2001 | Farhadi |
| 6,315,714 B1 | 11/2001 | Akiba |
| 6,319,197 B1 | 11/2001 | Tsuji et al. |
| 6,327,492 B1 | 12/2001 | Lemelson |
| 6,332,089 B1 | 12/2001 | Acker et al. |
| 6,348,058 B1 | 2/2002 | Melkent et al. |
| 6,352,503 B1 | 3/2002 | Matsui et al. |
| 6,364,876 B1 | 4/2002 | Erb et al. |
| 6,366,799 B1 | 4/2002 | Acker et al. |
| 6,371,907 B1 | 4/2002 | Hasegawa et al. |
| 6,402,687 B1 | 6/2002 | Ouchi |
| 6,408,889 B1 | 6/2002 | Komachi |
| 6,425,535 B1 | 7/2002 | Akiba |
| 6,428,203 B1 | 8/2002 | Danley |
| 6,428,470 B1 | 8/2002 | Thompson |
| 6,443,888 B1 | 9/2002 | Ogura et al. |
| 6,447,444 B1 | 9/2002 | Avni et al. |
| 6,453,190 B1 | 9/2002 | Acker et al. |
| 6,459,481 B1 | 10/2002 | Schaack |
| 6,468,203 B2 | 10/2002 | Belson |
| 6,468,265 B1 | 10/2002 | Evans et al. |
| 6,482,148 B1 | 11/2002 | Luke |
| 6,482,149 B1 | 11/2002 | Torii |
| 6,485,413 B1 | 11/2002 | Boppart et al. |
| 6,485,496 B1 | 11/2002 | Suyker et al. |
| 6,490,467 B1 | 12/2002 | Bucholz et al. |
| 6,503,259 B2 | 1/2003 | Huxel et al. |
| 6,511,417 B1 | 1/2003 | Taniguchi et al. |
| 6,511,418 B2 | 1/2003 | Shahidi et al. |
| 6,514,237 B1 | 2/2003 | Maseda |
| 6,517,477 B1 | 2/2003 | Wendlandt |
| 6,527,706 B2 | 3/2003 | Ide |
| 6,537,211 B1 | 3/2003 | Wang et al. |
| 6,544,215 B1 | 4/2003 | Bencini et al. |
| 6,547,723 B1 | 4/2003 | Ouchi |
| 6,554,793 B1 | 4/2003 | Pauker et al. |
| 6,569,084 B1 | 5/2003 | Mizuno et al. |
| 6,569,173 B1 | 5/2003 | Blatter et al. |
| 6,589,163 B2 | 7/2003 | Aizawa et al. |
| 6,610,007 B2 | 8/2003 | Belson et al. |
| 6,616,600 B2 | 9/2003 | Pauker |
| 6,638,213 B2 | 10/2003 | Ogura et al. |
| 6,641,528 B2 | 11/2003 | Torii |
| 6,650,920 B2 | 11/2003 | Schaldach et al. |
| 6,656,110 B1 | 12/2003 | Irion et al. |
| 6,664,718 B2 | 12/2003 | Pelrine et al. |
| 6,679,836 B2 | 1/2004 | Couvillon, Jr. et al. |
| 6,690,963 B2 | 2/2004 | Ben-Haim et al. |
| 6,699,183 B1 | 3/2004 | Wimmer |
| 6,719,685 B2 | 4/2004 | Fujikura et al. |
| 6,761,685 B2 | 7/2004 | Adams et al. |
| 6,783,491 B2 | 8/2004 | Saadat et al. |
| 6,790,173 B2 | 9/2004 | Saadat et al. |
| 6,793,621 B2 | 9/2004 | Butler et al. |
| 6,800,056 B2 | 10/2004 | Tartaglia et al. |
| 6,808,499 B1 | 10/2004 | Churchill et al. |
| 6,808,520 B1 | 10/2004 | Fourkas et al. |
| 6,817,973 B2 | 11/2004 | Merril et al. |
| 6,835,173 B2 | 12/2004 | Couvillon, Jr. |
| 6,837,846 B2 | 1/2005 | Jaffe et al. |
| 6,837,847 B2 | 1/2005 | Ewers et al. |
| 6,837,849 B2 | 1/2005 | Ogura et al. |
| 6,843,793 B2 | 1/2005 | Brock et al. |
| 6,850,794 B2 | 2/2005 | Shahidi |
| 6,858,005 B2 | 2/2005 | Ohline et al. |
| 6,869,396 B2 | 3/2005 | Belson |
| 6,875,170 B2 | 4/2005 | Francois et al. |
| 6,890,297 B2 | 5/2005 | Belson |
| 6,902,528 B1 | 6/2005 | Garibaldi et al. |
| 6,942,613 B2 | 9/2005 | Ewers et al. |
| 6,960,161 B2 | 11/2005 | Amling et al. |
| 6,960,162 B2 | 11/2005 | Saadat et al. |
| 6,960,163 B2 | 11/2005 | Ewers et al. |
| 6,974,411 B2 | 12/2005 | Belson |
| 6,984,203 B2 | 1/2006 | Tartaglia et al. |
| 6,997,870 B2 | 2/2006 | Couvillon, Jr. |
| 7,018,331 B2 | 3/2006 | Chang et al. |
| 7,044,907 B2 | 5/2006 | Belson |
| 7,087,013 B2 | 8/2006 | Belson et al. |
| 7,125,403 B2 | 10/2006 | Julian et al. |
| 7,167,180 B1 | 1/2007 | Shibolet |
| 7,285,088 B2 | 10/2007 | Miyake |
| 7,297,142 B2 | 11/2007 | Brock |
| 7,331,967 B2 | 2/2008 | Lee et al. |
| 7,371,210 B2 | 5/2008 | Brock et al. |
| 7,447,534 B1 | 11/2008 | Kingsley et al. |
| 8,062,212 B2 | 11/2011 | Belson |
| 8,226,546 B2 | 7/2012 | Belson |

(56) References Cited

U.S. PATENT DOCUMENTS

| | | | |
|---|---|---|---|
| 8,517,923 B2 | 8/2013 | Belson et al. | |
| 8,641,602 B2 | 2/2014 | Belson | |
| 8,721,530 B2* | 5/2014 | Ohline | A61B 1/0057 600/149 |
| 8,747,238 B2* | 6/2014 | Shelton, IV | A61B 34/37 464/57 |
| 8,827,894 B2 | 9/2014 | Belson | |
| 8,834,354 B2 | 9/2014 | Belson | |
| 8,845,524 B2 | 9/2014 | Belson et al. | |
| 8,888,688 B2 | 11/2014 | Julian et al. | |
| 9,138,132 B2 | 9/2015 | Belson | |
| 9,427,282 B2 | 8/2016 | Belson et al. | |
| 10,105,036 B2 | 10/2018 | Julian et al. | |
| 10,327,625 B2 | 6/2019 | Belson et al. | |
| 10,736,490 B2 | 8/2020 | Julian et al. | |
| 2001/0031983 A1* | 10/2001 | Brock | A61B 34/30 606/205 |
| 2001/0041887 A1 | 11/2001 | Crowley | |
| 2002/0016607 A1 | 2/2002 | Bonadio et al. | |
| 2002/0022829 A1 | 2/2002 | Nagase et al. | |
| 2002/0032437 A1 | 3/2002 | Andrews et al. | |
| 2002/0045778 A1 | 4/2002 | Murahashi et al. | |
| 2002/0120252 A1* | 8/2002 | Brock | A61B 90/36 606/1 |
| 2002/0129508 A1 | 9/2002 | Blattner et al. | |
| 2002/0130673 A1 | 9/2002 | Pelrine et al. | |
| 2002/0151767 A1 | 10/2002 | Sonnenschein et al. | |
| 2002/0169361 A1 | 11/2002 | Taniguchi et al. | |
| 2002/0177843 A1* | 11/2002 | Anderson | A61B 34/37 606/1 |
| 2002/0183592 A1 | 12/2002 | Suzuki et al. | |
| 2003/0065373 A1 | 4/2003 | Lovett et al. | |
| 2003/0073992 A1 | 4/2003 | Sliwa et al. | |
| 2003/0083550 A1 | 5/2003 | Miyagi | |
| 2003/0130598 A1 | 7/2003 | Manning et al. | |
| 2003/0163128 A1 | 8/2003 | Patil et al. | |
| 2003/0167007 A1 | 9/2003 | Belson | |
| 2003/0182091 A1 | 9/2003 | Kukuk | |
| 2003/0187460 A1 | 10/2003 | Chin et al. | |
| 2003/0195387 A1 | 10/2003 | Kortenbach et al. | |
| 2003/0233056 A1 | 12/2003 | Saadat et al. | |
| 2003/0236455 A1 | 12/2003 | Swanson et al. | |
| 2003/0236505 A1 | 12/2003 | Bonadio et al. | |
| 2003/0236549 A1 | 12/2003 | Bonadio et al. | |
| 2004/0019254 A1 | 1/2004 | Belson et al. | |
| 2004/0044270 A1 | 3/2004 | Barry | |
| 2004/0049251 A1 | 3/2004 | Knowlton | |
| 2004/0097788 A1 | 5/2004 | Mourlas et al. | |
| 2004/0106852 A1 | 6/2004 | Windheuser et al. | |
| 2004/0111081 A1* | 6/2004 | Whitman | A61B 17/00 606/1 |
| 2004/0176683 A1 | 9/2004 | Whitin et al. | |
| 2004/0186350 A1 | 9/2004 | Brenneman et al. | |
| 2004/0193008 A1 | 9/2004 | Jaffe et al. | |
| 2004/0193009 A1 | 9/2004 | Jaffe et al. | |
| 2004/0210109 A1 | 10/2004 | Jaffe et al. | |
| 2004/0220450 A1 | 11/2004 | Jaffe et al. | |
| 2004/0230096 A1 | 11/2004 | Stefanchik et al. | |
| 2005/0085693 A1 | 4/2005 | Belson et al. | |
| 2005/0124855 A1 | 6/2005 | Jaffe et al. | |
| 2005/0137454 A1 | 6/2005 | Saadat et al. | |
| 2005/0137455 A1 | 6/2005 | Ewers et al. | |
| 2005/0137456 A1 | 6/2005 | Saadat et al. | |
| 2005/0154258 A1 | 7/2005 | Tartaglia et al. | |
| 2005/0154261 A1 | 7/2005 | Ohline et al. | |
| 2005/0165276 A1 | 7/2005 | Belson et al. | |
| 2005/0168571 A1 | 8/2005 | Lia et al. | |
| 2005/0187576 A1* | 8/2005 | Whitman | A61B 17/1155 227/176.1 |
| 2005/0203339 A1 | 9/2005 | Butler et al. | |
| 2005/0209506 A1 | 9/2005 | Butler et al. | |
| 2005/0222497 A1 | 10/2005 | Belson | |
| 2005/0250990 A1 | 11/2005 | Le et al. | |
| 2006/0009678 A1 | 1/2006 | Jaffe et al. | |
| 2006/0015009 A1 | 1/2006 | Jaffe et al. | |
| 2006/0015010 A1 | 1/2006 | Jaffe et al. | |
| 2006/0089528 A1 | 4/2006 | Tartaglia et al. | |
| 2006/0089529 A1 | 4/2006 | Tartaglia et al. | |
| 2006/0089530 A1 | 4/2006 | Tartaglia et al. | |
| 2006/0089531 A1 | 4/2006 | Tartaglia et al. | |
| 2006/0089532 A1 | 4/2006 | Tartaglia et al. | |
| 2006/0100642 A1 | 5/2006 | Yang et al. | |
| 2006/0235457 A1 | 10/2006 | Belson | |
| 2006/0235458 A1 | 10/2006 | Belson | |
| 2006/0258912 A1 | 11/2006 | Belson et al. | |
| 2006/0259029 A1 | 11/2006 | Utley et al. | |
| 2007/0043259 A1 | 2/2007 | Jaffe et al. | |
| 2007/0055219 A1* | 3/2007 | Whitman | A61B 17/1285 606/1 |
| 2007/0093858 A1 | 4/2007 | Gambale et al. | |
| 2007/0135803 A1 | 6/2007 | Belson | |
| 2007/0161291 A1 | 7/2007 | Swinehart et al. | |
| 2007/0161857 A1 | 7/2007 | Durant et al. | |
| 2007/0249901 A1 | 10/2007 | Ohline et al. | |
| 2007/0270650 A1 | 11/2007 | Eno et al. | |
| 2008/0045794 A1 | 2/2008 | Belson | |
| 2008/0154288 A1 | 6/2008 | Belson | |
| 2008/0214893 A1 | 9/2008 | Tartaglia et al. | |
| 2008/0248215 A1 | 10/2008 | Sauer et al. | |
| 2009/0099420 A1 | 4/2009 | Woodley et al. | |
| 2009/0216083 A1 | 8/2009 | Durant et al. | |
| 2010/0094088 A1 | 4/2010 | Ohline et al. | |
| 2011/0065993 A1 | 3/2011 | Belson et al. | |
| 2012/0041262 A1 | 2/2012 | Belson | |
| 2012/0100729 A1* | 4/2012 | Edidin | H01R 13/622 439/38 |
| 2015/0005576 A1 | 1/2015 | Belson et al. | |
| 2015/0320295 A1 | 11/2015 | Belson et al. | |
| 2015/0359414 A1 | 12/2015 | Belson | |
| 2017/0020615 A1 | 1/2017 | Koenig et al. | |
| 2019/0069763 A1 | 3/2019 | Julian et al. | |
| 2019/0365205 A1 | 12/2019 | Belson et al. | |

FOREIGN PATENT DOCUMENTS

| | | |
|---|---|---|
| DE | 4102211 A1 | 8/1991 |
| DE | 19626433 A1 | 1/1998 |
| DE | 19729499 A1 | 1/1999 |
| EP | 0165718 A2 | 12/1985 |
| EP | 382974 A1 | 8/1990 |
| EP | 0497781 B1 | 1/1994 |
| EP | 0993804 A1 | 4/2000 |
| EP | 1101442 A2 | 5/2001 |
| EP | 1681013 A1 | 7/2006 |
| ES | 2048086 A | 3/1994 |
| ES | 2062930 A | 12/1994 |
| FR | 2732225 A1 | 10/1996 |
| FR | 2807960 A1 | 10/2001 |
| GB | 2347685 A | 9/2000 |
| IE | 20000559 | 7/2000 |
| IE | 20020170 | 3/2002 |
| JP | 4712705 | 5/1972 |
| JP | 61205912 A | 9/1986 |
| JP | 63136014 A2 | 6/1988 |
| JP | 63272322 A2 | 11/1988 |
| JP | S63503365 A | 12/1988 |
| JP | 1152413 A2 | 6/1989 |
| JP | H01153292 A | 6/1989 |
| JP | 1229220 A2 | 9/1989 |
| JP | 1262372 A2 | 10/1989 |
| JP | 2246986 A2 | 10/1990 |
| JP | 2296209 A2 | 12/1990 |
| JP | 3004830 A2 | 1/1991 |
| JP | 3109021 A2 | 5/1991 |
| JP | 3136630 A2 | 6/1991 |
| JP | 3139325 A2 | 6/1991 |
| JP | 3170125 A2 | 7/1991 |
| JP | 4002322 A | 1/1992 |
| JP | 4054970 A2 | 2/1992 |
| JP | 5001999 A2 | 1/1993 |
| JP | 5011196 A2 | 1/1993 |
| JP | 5111458 A2 | 5/1993 |
| JP | 5177002 A2 | 7/1993 |

(56) References Cited

FOREIGN PATENT DOCUMENTS

| | | |
|---|---|---|
| JP | 5184531 A2 | 7/1993 |
| JP | 5305073 A2 | 11/1993 |
| JP | 6007287 A2 | 1/1994 |
| JP | H0670940 A | 3/1994 |
| JP | H06142106 A | 5/1994 |
| JP | H06285009 A | 10/1994 |
| JP | H06285043 A | 10/1994 |
| JP | H06510439 A | 11/1994 |
| JP | 7088788 A2 | 4/1995 |
| JP | 7116104 A2 | 5/1995 |
| JP | 7120684 A2 | 5/1995 |
| JP | 8010336 A2 | 1/1996 |
| JP | 8066351 A2 | 3/1996 |
| JP | 8322783 A2 | 12/1996 |
| JP | 8322786 A2 | 12/1996 |
| JP | 9028662 A2 | 2/1997 |
| JP | 10014863 A2 | 1/1998 |
| JP | 10337274 A2 | 12/1998 |
| JP | 11042258 A2 | 2/1999 |
| JP | 11048171 A | 2/1999 |
| JP | H11509436 A | 8/1999 |
| JP | H11313827 A | 11/1999 |
| JP | 2000279367 A | 10/2000 |
| JP | 21046318 A2 | 2/2001 |
| JP | 21096478 A2 | 4/2001 |
| JP | 2001519199 A | 10/2001 |
| JP | 2001521773 A | 11/2001 |
| JP | 2002017746 A | 1/2002 |
| JP | 2002113036 A | 4/2002 |
| JP | 3322356 | 9/2002 |
| JP | 2002264048 A | 9/2002 |
| JP | 2002531164 A | 9/2002 |
| JP | 2003504148 A | 2/2003 |
| JP | 2003525688 A | 9/2003 |
| JP | 2003528677 A | 9/2003 |
| JP | 2005507731 A | 3/2005 |
| SU | 871786 A1 | 10/1981 |
| SU | 1256955 A1 | 9/1986 |
| SU | 1301701 A1 | 4/1987 |
| WO | WO-199219147 A1 | 11/1992 |
| WO | WO-9315648 A1 | 8/1993 |
| WO | WO-199317751 A1 | 9/1993 |
| WO | WO-199419051 A1 | 9/1994 |
| WO | WO-199504556 A2 | 2/1995 |
| WO | WO-9509562 A1 | 4/1995 |
| WO | WO-9605768 A1 | 2/1996 |
| WO | WO-9639963 A1 | 12/1996 |
| WO | WO-199710746 A1 | 3/1997 |
| WO | WO-9725101 A2 | 7/1997 |
| WO | WO-9729701 A1 | 8/1997 |
| WO | WO-9729710 A1 | 8/1997 |
| WO | WO-199811816 A1 | 3/1998 |
| WO | WO-199824017 A2 | 6/1998 |
| WO | WO-9849938 A1 | 11/1998 |
| WO | WO-199916359 A1 | 4/1999 |
| WO | WO-199933392 A1 | 7/1999 |
| WO | WO-199951283 A2 | 10/1999 |
| WO | WO-199959664 A1 | 11/1999 |
| WO | WO-0010456 A1 | 3/2000 |
| WO | WO-200010466 A1 | 3/2000 |
| WO | WO-200027462 A1 | 5/2000 |
| WO | WO-200054653 A1 | 9/2000 |
| WO | WO-200074565 A1 | 12/2000 |
| WO | WO-200149353 A2 | 7/2001 |
| WO | WO-200158973 A2 | 8/2001 |
| WO | WO-200167964 A2 | 9/2001 |
| WO | WO-200170096 A1 | 9/2001 |
| WO | WO-200170097 A1 | 9/2001 |
| WO | WO-0174235 A1 | 10/2001 |
| WO | WO-200180935 A1 | 11/2001 |
| WO | WO-200224058 A2 | 3/2002 |
| WO | WO-200239909 A1 | 5/2002 |
| WO | WO-200247549 A1 | 6/2002 |
| WO | WO-200264028 A1 | 8/2002 |
| WO | WO-200268988 A1 | 9/2002 |
| WO | WO-200269841 A2 | 9/2002 |
| WO | WO-200289692 A1 | 11/2002 |
| WO | WO-200296276 A1 | 12/2002 |
| WO | WO-03028547 A2 | 4/2003 |
| WO | WO-03073920 A2 | 9/2003 |
| WO | WO-200373921 A1 | 9/2003 |
| WO | WO-03086498 A2 | 10/2003 |
| WO | WO-03092476 A2 | 11/2003 |
| WO | WO-2004000403 A1 | 12/2003 |
| WO | WO-200406980 A2 | 1/2004 |
| WO | WO-2004019769 A1 | 3/2004 |
| WO | WO-2004049905 A2 | 6/2004 |
| WO | WO-200471284 A1 | 8/2004 |
| WO | WO-200480313 A1 | 9/2004 |
| WO | WO-2004084702 A2 | 10/2004 |
| WO | WO-2005072445 A2 | 8/2005 |
| WO | WO-2005084542 A1 | 9/2005 |
| WO | WO-2006136827 A1 | 12/2006 |
| WO | WO-2015175200 A1 | 11/2015 |
| WO | WO-2016043845 A1 | 3/2016 |
| WO | WO-2016183054 A1 | 11/2016 |
| WO | WO-2016205452 A1 | 12/2016 |

OTHER PUBLICATIONS

Bar-Cohen, J., "EAP applications, potential, and challenges," Chapter 21 in Electroactive Polymer (EAP) Actuators as Artificial Muscles, Bar-Cohen, Ed., SPIE Press, 2001, pp. 615-659.

Bar-Cohen, Y., "EAP history, current status, and infrastructure," Chapter 1 in Electroactive Polymer (EAP) Actuators as Artificial Muscles, Bar-Cohen Ed., SPIE Press, 2001, pp. 3-44.

Bar-Cohen, Y. Ed., Worldwide ElectroActive Polymers (Artificial Muscles) Newsletter, Jun. 2001, vol. 3, issue 1, pp. 1-14.

Bar-Cohen, Y., "Transition of EAP material from novelty to practical applications—are we there yet" Smart Structures and Materials 2001: Electroactive Polymer Actuators and Devices, Yoseph Bar-Cohen Ed., Proceedings of SPIE, Mar. 5-8, 2001, vol. 4329, pp. 1-6.

Berger, W. L. et al., "Sigmoid Stiffener for Decompression Tube Placement in Colonic Pseudo-Obstruction," Endoscopy, 2000, vol. 32, Issue 1, pp. 54-57.

Brock, D.L., "Review of artificial muscle based on contractile polymers," MIT Artificial Intelligence Laboratory, A.I.Memo No. 1330, Nov. 1991, 10 pages. Accessed Jun. 23, 2005. Internet: http://www.ai.mit.edu/projects/muscle/papers/memo1330/memo1330.html.

Cho, S. et al., "Development of micro inchworm robot actuated by electrostrictive polymer actuator," Smart Structures and Materials 2001: Electroactive Polymer Actuators and Devices, Yoseph Bar-Cohen Ed., Proceedings of SPIE, Mar. 5-8, 2001, vol. 4329, pp. 466-474.

Office Action issued in corresponding Japanese Application No. P2006-551580, Dispatch Date: Aug. 21, 2012, Dispatch No. 568236.

Duntgen, C., "Walking machines: 0-legged-robots: A compilation by Christian Duntgen," Aug. 26, 2000, 16 pages.

EP03791924 Supplementary Partial Search Report, dated Feb. 27, 2009, 4 pages.

EP11175098 Extended EP Search Report mailed Dec. 1, 2011, 7 pages. (NEOG704-505D1/EP).

European Search Report for Application No. EP05002014, mailed on Mar. 31, 2005, 3 pages (NEOG704-201DIV/EP).

Extended European Search Report for Application No. EP05824444, mailed on Apr. 13, 2011, 6 pages (NEOG709-501/EP).

Grecu, E. et al., "Snake-like flexible Micro-robot," Copernicus project presentation, financed by European Community, Project start May 1, 1995, 6 pages. Accessed Dec. 27, 2001; Internet: http://www.agip.sciences.univ-metz.fr/~mihalach/Copernicus_project_engl.html.

Hasson, H.M., "Technique of Open Laparoscopy," (from step 1 to step 9), May 1979, 2424 North Clark Street, Chicago, Illinois 60614, 3 pages.

Ikuta, Koji et al., "Shape memory alloy servo actuator system with electric resistance feedback and application for active endoscope," Proc. IEEE International Conference on Robotics and Automation, 1988, pp. 427-430, vol. 1, IEEE.

(56) References Cited

OTHER PUBLICATIONS

International Preliminary Examination Report for Application No. PCT/US2001/10907, mailed on Jan. 21, 2003, 3 pages (NEOG704-201/PCT).
International Search Report and Written Opinion for Application No. PCT/US2004/026948, mailed on Dec. 29, 2005, 4 pages (NEOG712-101/PCT).
International Search Report and Written Opinion for Application No. PCT/US2005/03140, mailed on May 6, 2008, 6 pages (NEOG711-201/PCT).
International Search Report for Application No. PCT/US2001/10907, mailed on Aug. 28, 2001, 3 pages.
Ireland Application No. 2000/0225 filed on Mar. 22, 2000, Inventor Declan B., et al.
Jager, E.W.H. et al., "Microfabricating conjugated polymer actuators," Science, Nov. 24, 2000, vol. 290, pp. 1540-1545.
Japanese application No. 2007-541342 Office Action dated May 17, 2011, 7 pages, including translation.
Japanese Notice of Reasons for Rejection for Patent Application No. JP2014-249104 dated Oct. 30, 2015.
Jeon, J.W. et al., "Electrostrictive polymer actuators and their control systems," Smart Structures and Materials 2001: Electroactive Polymer Actuators and Devices, Yoseph Bar-Cohen Ed., Proceedings of SPIE, Mar. 5-8, 2001, vol. 4329, pp. 380-388.
Klaassen, B., "GMD-SNAKE: Robot snake with a flexible real-time control," AiS—GMD—Snake, last updated Oct. 17, 2001, 3 pages, accessed Dec. 27, 2001; Internet: http://ais.gmd.de/BAR/snake.html.
Kornbluh, R. et al., "Application of dielectric elastomer EAP actuators, "Chapter 16 in Electroactive Polymer (EAP) Actuators as Artificial Muscles, Yoseph Bar-Cohen, Ed., SPIE Press, 2001, pp. 457-495.
Kubler, C. et al., "Endoscopic robots,"Proceedings of 3rd International Conference on Medical Image Computing and Computer-Assisted Intervention (MICCAI 2000), Oct. 11-14, 2000, in Lecture Notes in Computer Science, Springer, vol. 1935, pp. 949-955.
Laptop Magazine, Science & Technology section, Oct. 2002, pp. 98, 100, and 102.
Lee, Thomas S. et al., "A highly redundant robot system for inspection," Proceedings of Conference on Intelligent Robotics in Field, Factory, Service, and Space (CIRFFSS '94). Mar. 21-24, 1994. vol. 1, pp. 142-148. Houston, Texas.
Lightdale, C.J., "New developments in endoscopy," American College of Gastroenterology 65th Annual Scientific Meeting, Day 1, Oct. 16, 2000, pp. 1-9.
Madden, J.D.W., Abstract of "Conducting polymer actuators," Smart Structures and Materials 2001: Electroactive Polymer Actuators and Devices, Yoseph Bar-Cohen Ed., Proceedings of SPIE, Mar. 5-8, 2001, vol. 4329, 1 page.
Madden, J.D.W. et al., "Polypyrrole actuators: modeling and performance", Smart Structures and Materials 2001: Electroactive Polymer Actuators and Devices, Yoseph Bar-Cohen Ed., Proceedings of SPIE, Mar. 5-8, 2001, vol. 4329, pp. 72-83.
Mazzoldi, A., "Smart Catheters," Internet: http://www.piaggio.ccii.unipi.it/cathe.htm, printed Aug. 27, 2001, 2 pages.

McKernan, J.B. et al., "Laparoscopic general surgery," Journal of the Medical Association of Georgia, Mar. 1990, vol. 79, Issue 3, pp. 157-159.
Nam, J.D., "Electroactive polymer (EAP) actuators and devices for micro-robot systems," Nov. 28, 2000, 1 page.
Office Action mailed Jul. 30, 2013 for Japanese Application No. 20110200974 filed Sep. 14, 2011 (NEOG711-201D1/JP).
PCT/US02/29472 International Search Report, mailed on Mar. 6, 2003, 3 pages (NEOG704-501/PCT).
PCT/US03/06078 International Search Report, mailed on Aug. 13, 2003, 1 page (NEOG704-502/PCT).
PCT/US03/13600 International Search Report, mailed on Dec. 12, 2003, 1 page (NEOG704-504/PCT).
PCT/US03/27042 International Search Report, mailed on Feb. 4, 2004, 2 pages (NEOG704-505/PCT).
PCT/US03/37778 International Search Report, mailed on Feb. 8, 2005, 1 page (NEOG704-506/PCT).
PCT/US2005/040893 International Search Report and Written Opinion of the International Searching Authority, mailed Jun. 23, 2008, 5 pages.
Peirs, J. et al., "Miniature parallel manipulators for integration in a self-propelling endoscope," IUAP P4/24 IMechS Workshop, Organized by UCL/PRM, Oct. 27, 1999, 2 pages.
Pelrine, R. et al., "Applications of dielectric elastomer actuators," Smart Structures and Materials 2001: Electroactive Polymer Actuators and Devices, Yoseph Bar-Cohen Ed., Proceedings of SPIE, Mar. 5-8, 2001, vol. 4329, Issue 1, pp. 335-349.
Sansinena, J.M. et al., "Conductive polymers," Chapter 7 of Electroactive Polymer (EAP) Actuators as Artificial Muscles, Bar-Cohen Ed., SPIE Press, 2001, pp. 193-221.
Slatkin, A.B. et al., "The development of a robotic endoscope," Proceedings 1995 IEEE/RSJ International Conference on Intelligent Robots and Systems, Aug. 5-9, 1995, vol. 2, pp. 162-171, Pittsburgh, Pennsylvania.
Summons to Attend Oral Proceedings mailed Mar. 31, 2016 for European Application No. 05824444.3 filed Nov. 8, 2005, 5 pages (NEOG709-501/EP).
Supplementary European Search Report for Application No. EP03790076, mailed on Dec. 28, 2007, 4 pages (NEOG704-506/EP).
Supplementary European Search Report for Application No. EP04781605, mailed on Jul. 23, 2010, 3 pages (NEOG712-101/EP).
Supplementary European Search Report for Application No. EP05712548, mailed on Jul. 6, 2012, 3 pages.
Supplementary European Search Report of EP Patent Application No. EP03728638, dated Oct. 27, 2005, 2 pages total. (NEOG704-504/EP).
U.S. Appl. No. 12/425,272 Office Action, filed Mar. 11, 2011, 7 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Zuccaro, G., "Procedural sedation in the GI suite," A conference co-sponsored by the American Society of Anesthesiologists, 16th Annual Meeting 2001, May 3-6, 2001, pp. 162-171.

* cited by examiner

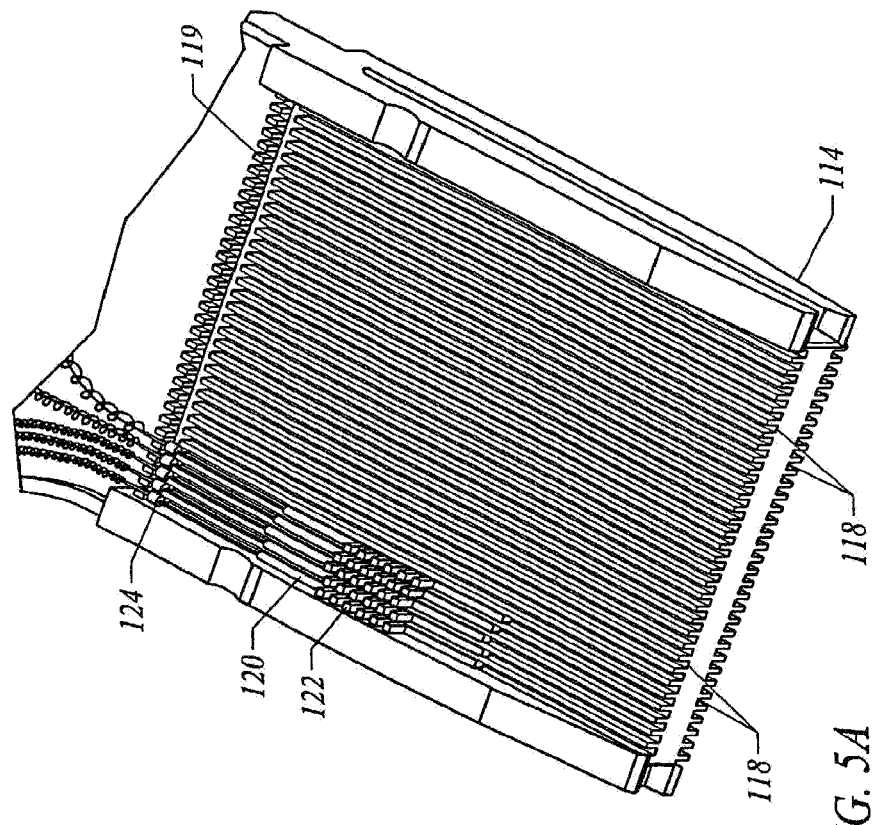
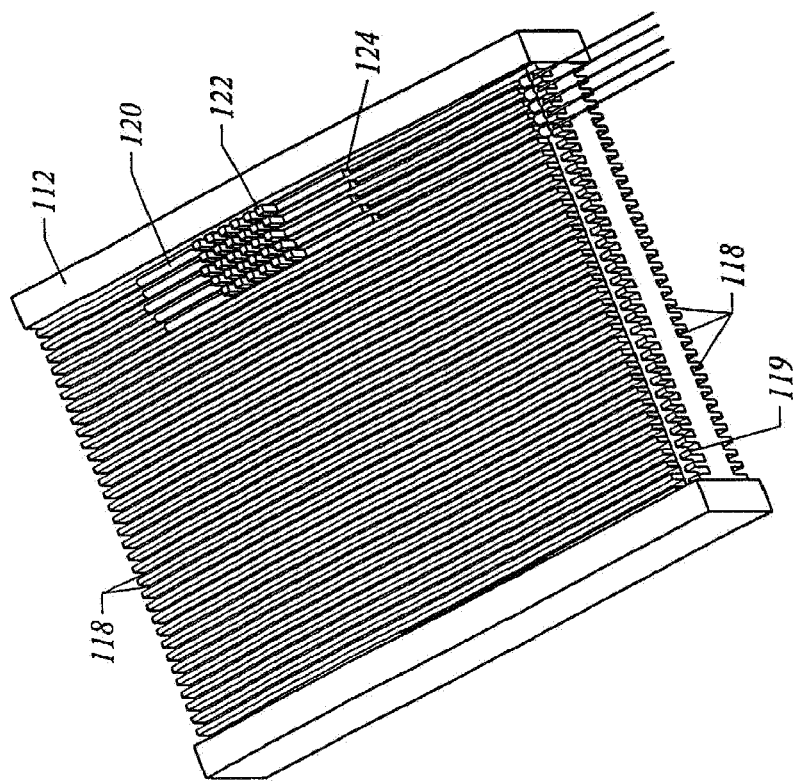
FIG. 5A

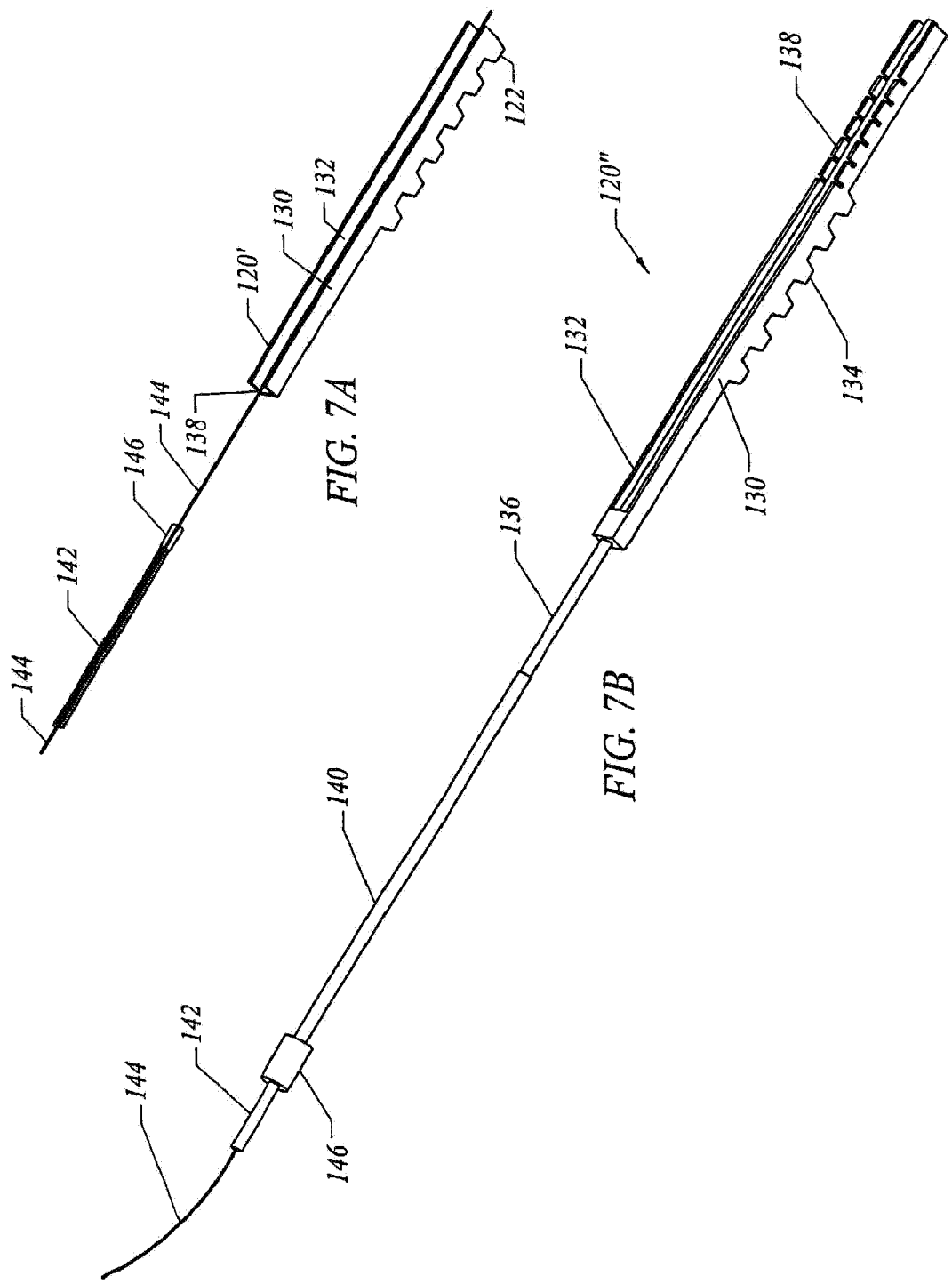

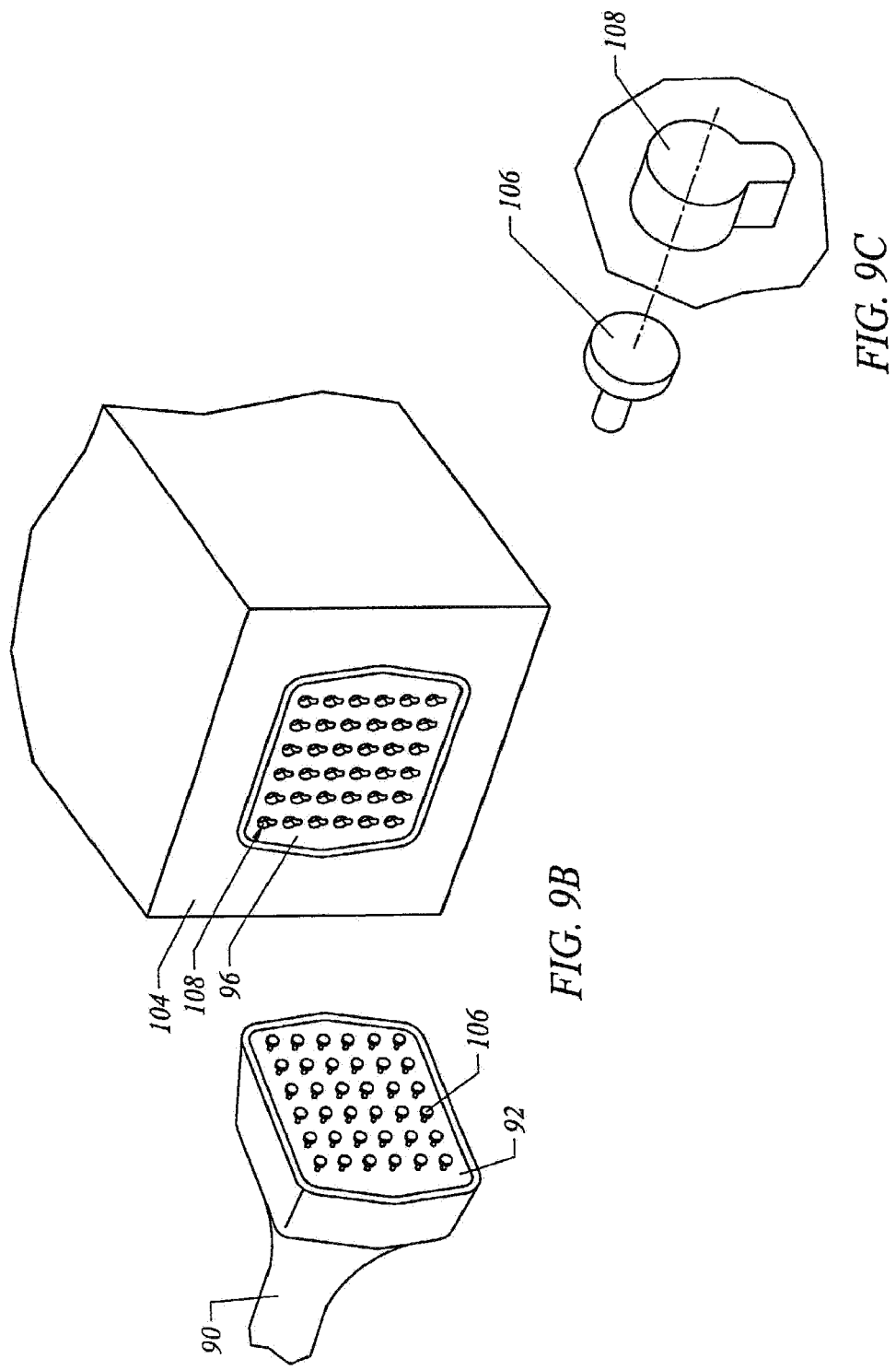

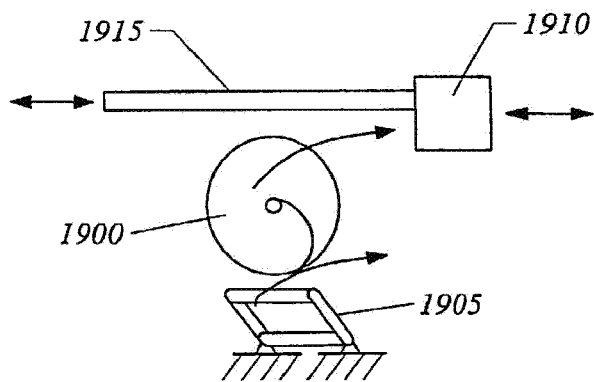
FIG. 19
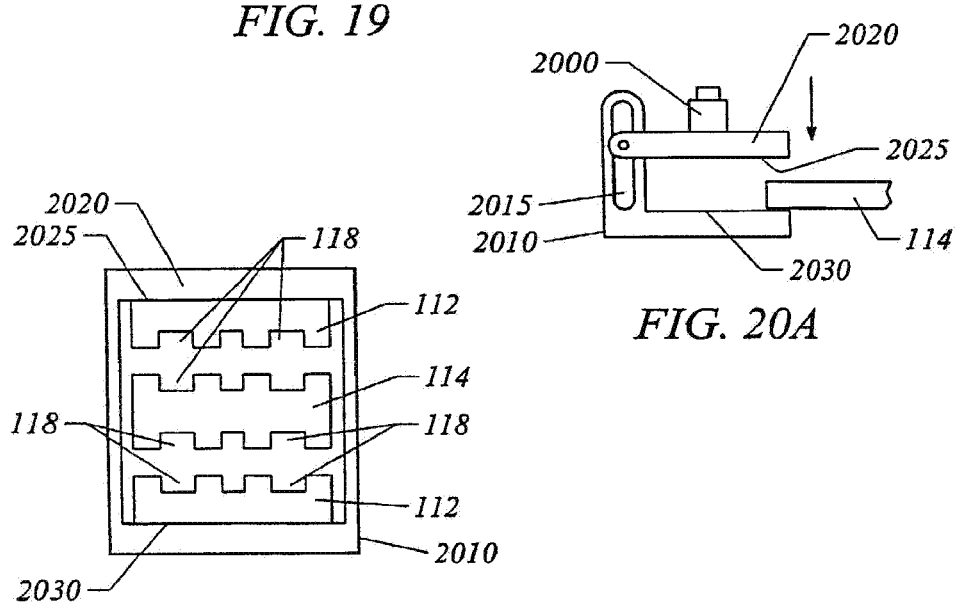
FIG. 20A
FIG. 20B
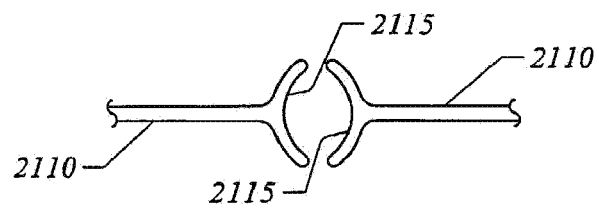
FIG. 21

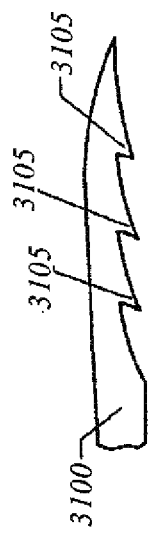
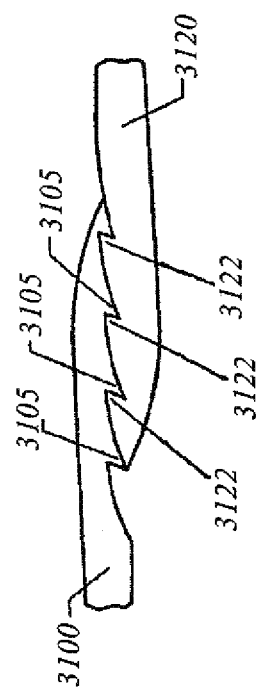
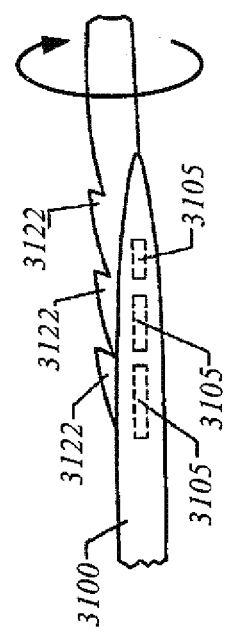
FIG 31A
FIG 31B
FIG 31C

CONNECTOR DEVICE FOR A CONTROLLABLE INSTRUMENT

CROSS REFERENCE TO RELATED APPLICATIONS

This application is a continuation of U.S. application Ser. No. 16/123,309 (now U.S. Pat. No. 10,736,490), filed Sep. 6, 2018, which is a continuation of U.S. application Ser. No. 14/537,127, filed Nov. 10, 2014 (now U.S. Pat. No. 10,105,036), which is a continuation of U.S. application Ser. No. 10/988,212, filed Nov. 12, 2004, (now U.S. Pat. No. 8,888,688), each of which is incorporated herein by reference in its entirety.

FIELD OF THE INVENTION

The present invention relates generally to connector assemblies for use with articulating instruments. More particularly, it relates to connectors and systems for transmitting force to an articulating instrument to move that instrument.

BACKGROUND OF THE INVENTION

One challenge confronting the use of articulating instruments is the efficient and reliable coupling of the force generated for moving the articulating components of the instrument to the articulating components themselves. It may be desirable to have a single force generator that may be used with a number of individual articulating instruments. In this case, the ability to switch, with ease, between the different individual articulating instruments is desirable. For example, while one articulating instrument is being cleaned or maintained, the force generator could be coupled to another articulating instrument thereby increasing the utilization factor of the force generator.

As the degree of movement and control for an articulating instrument increases, the number, variety and size of articulating components needed to operate the instrument increases. As the variety and size of articulating components increases, so too increases the number of force transmission elements to move those articulating components. As such, there also exists a need for a connector that provides an organized arrangement of the force transmission elements in an effort to reduce complexity at the force transmission/component articulation interface.

Articulating instruments are used in a wide variety of commercial settings including, for example, industrial robotic applications and medical applications. One example of an articulating medical instrument is an endoscope. An endoscope is a medical instrument for visualizing the interior of a patient's body. Endoscopes are used for a variety of different diagnostic and interventional procedures, including colonoscopy, bronchoscopy, thoracoscopy, laparoscopy and video endoscopy. The desire to access remote portions of the body more efficiently or access one area of the body while avoiding other areas along the way increases the complexity of articulating endoscopes and articulating surgical instruments generally.

Insertion of an articulating colonoscope is further complicated by the fact that the colon represents a tortuous and convoluted path. Considerable manipulation of the colonoscope by manipulation of articulating components is often necessary to advance the colonoscope through the colon. However, as the colonoscope is inserted farther into the colon, it becomes more difficult to advance the colonoscope along the selected path. At each turn of the colon, the colonoscope rubs against the mucosal surface of the colon and friction and slack in the articulating components of the colonoscope changes. As such, there also exists a need to provide compensation for changes in the friction and slack of the articulating components as the colonoscope is advanced or withdrawn from the colon.

As such, a need exists for connector assemblies that will organize and simplify the process of connecting the plurality of elements needed to move and control an articulating instrument with the force generator or actuators that generate the forces to move the articulating instrument.

SUMMARY OF THE INVENTION

In one aspect of the present invention, there is a system for moving a controllable article. The system includes a force generator; a first force transmission element having a first end connected to the force generator and a second end having a first connecting element; a second force transmission element having a first end connected to the controllable article and a second end having a second connecting element; and a connector for releasably engaging the first connecting element and the second connecting element. In one aspect of the present invention, the connector releasably engages the first connecting element and the second connecting element using a mechanical coupler.

In one aspect of the present, invention, the force generator generates a mechanical force. In another aspect of the present invention, the force generator generates a hydraulic force. In another aspect of the present invention, the force generator generates a rotational force. In another aspect of the present invention, the rotational force from the force generator is translated into longitudinal motion within the connector. In another aspect of the present invention, the force generator generates a pneumatic force.

In one aspect of the present invention provides a connector having a first portion releasably coupled to a second portion. The first portion has a plurality of guideways. Each of the guideways has a carriage assembly and each of the carriage assemblies is coupled to a force generator. The second portion also has a plurality of guideways where each of the guideways has a carriage assembly. Each of the carriage assemblies in the second portion is coupled to an article articulated by moving one or more of the second portion carriage assemblies. In one aspect of the present invention, the plurality of guideways in the first and/or second portion are parallel. In another aspect of the present invention each of the plurality of guideways in the first portion are parallel to each of the plurality of guideways in the second portion. In another aspect, at least one of the plurality of guideways in the first portion is aligned with at least one of the plurality of guideways in the second portion.

In one aspect of the invention, the force generated by the force generator is coupled to the article.

In another aspect of the invention, at least one carriage assembly in the first portion is engaged with at least one carriage assembly in the second portion. In one aspect, the engaging feature and the complementary engaging feature are engaged by relative movement between the first connector portion and the second connector portion. In another aspect, a carriage assembly of the first portion has an engaging feature and a carriage assembly of the second portion has an engaging feature complementary to the engaging feature of the carriage assembly of the first portion. In one aspect, the engaging feature and the complementary engaging feature include teeth. In another aspect, the engaging feature and the complementary engaging feature include gear teeth. In another aspect, the engaging feature and the complementary engaging feature include a spur gear. In another aspect, the engaging feature and the complementary engaging feature include a shape memory alloy element. In another aspect, the engaging feature and the complementary engaging feature include hooks. In another aspect, the engaging feature and the complementary engaging feature are threaded members. In another aspect, the engaging feature and the complementary engaging feature comprise a slot and pin. In another aspect, the engaging feature and the complementary engaging feature comprise a spline and a rack.

In another aspect, a force generated by the force generator is transmitted to the article when the first portion is coupled to the second portion. In another aspect, the first portion is coupled to the second portion using a lever. In another aspect, the first portion is coupled to the second portion by hydraulically moving one or both of the first portion or the second portion. In another aspect, the first portion is coupled to the second portion by pneumatically moving one or both of the first portion or the second portion. In another aspect, the first portion is coupled to the second portion by moving one or both of the first portion and the second portion utilizing a lead screw, a motor driven lead screw and combinations thereof.

In one specific embodiment, the force generator is a motor. The motor is coupled to a leadscrew assembly, so that when the motor rotates, it transmits torque to the leadscrew. A modified nut on the leadscrew is constrained to prevent rotational motion, so that when the leadscrew is rotated, the nut is translated along the axis of the leadscrew. The torque from the motor is thereby translated into linear motion. In this specific embodiment, a force transmission element is a cable that is connected to the nut on one end and a carriage assembly on the other end. The linear motion of the nut translates into force on the cable. In the present embodiment, 64 of the leadscrew assemblies are arranged in modules for easy organization and maintenance. The modules are supported in a chassis that also houses the first portion of the connector as described herein.

In one aspect, the article is an endoscope. In another aspect, the article is a control surface. In another aspect, the article is a robot. In another aspect, the article is a surgical instrument.

In one aspect, the carriage assemblies are biased to an initial condition. In another aspect, a biasing element is coupled to each one of the plurality of carriage assemblies. In yet another aspect, the carriage assemblies are aligned before engaging the first connector portion and the second connector portion. In yet another aspect, a biasing element aligns the carriage assemblies before engaging the first connector portion and the second connector portion.

In yet another aspect of the invention, a connector for coupling a force to move an article is provided. The connector has a first connector housing having a plurality of guideways and a carriage assembly disposed in each guideway. A force transmission element attached to each carriage assembly. The force transmission elements are adapted for connection to a force generator. A second connector housing having a plurality of guideways and a carriage assembly disposed in each guideway. A force transmission element attached to each carriage assembly. The force transmission elements are adapted for connection to an article. In one aspect, the article is a surgical instrument. In another aspect, the article is an endoscope In one aspect, at least one of the first connector housing and the second connector housing comprising a slack area.

In another aspect, the slack area contains the force transmission elements of the first connector housing arranged in an angular relationship to the guideways in the first connector housing. In yet another aspect, the slack area contains the force transmission elements of the second connector housing arranged in an angular relationship to the guideways in the second connector housing.

In yet another aspect, the connector includes a sensor to detect an operational characteristic of the connector. In one aspect, the operational characteristic of the connector is the engagement of a carriage assembly in the first connector housing to a carriage assembly in the second connector housing. In another aspect, the operational characteristic of the connector is the disengagement of a carriage assembly in the first connector housing to a carriage assembly in the second connector housing. In yet another aspect, the operational characteristic of the connector is the tension in a force transmission element or a position of each or any of the carriage assemblies. In yet another aspect, the operational characteristic of the connector is the torque exerted on a force transmission element. In yet another aspect, the operational characteristic of the connector is a force acting on a force transmission element. In yet another aspect, the operational characteristic of the connector is the time in service of a particular article. In yet another aspect, the operational characteristic of the connector is the range of travel of a carriage assembly. In another aspect, the operational characteristic of the connector is the engagement of a carriage assembly in the first connector housing to a carriage assembly in the second connector housing.

One aspect of the invention is a connection assembly for connecting an articulating instrument to a force generator. The connection assembly has a first portion releasably coupled to a second portion. The first portion includes at least one guideway, a carriage assembly moveable relative to the at least one guideway. A force transmission element is attached to the carriage assembly and coupled to the force generator. The second portion includes at least one guideway, a carriage assembly moveable relative to the at least one guideway. A force transmission element is attached to the carriage assembly and coupled to the articulating instrument. In one aspect, the carriage assembly of the first portion engages the carriage assembly of the second portion when the first portion is coupled to the second portion. In another aspect, the first portion is coupled to the second portion using a first motion and the carriage assembly of the first portion engages the carriage assembly of the second portion using a second motion. In yet another aspect, movement of a carriage assembly in the first portion relative to the at least one guideway in the first portion moves the articulating instrument when the first portion is coupled to the second portion.

In yet another aspect, a carriage assembly of the first portion is engaged to a carriage assembly of the second portion using hooks. In yet another aspect, a carriage assembly of the first portion is engaged to a carriage assembly of the second portion using gears. In yet another aspect, a carriage assembly of the first portion is engaged to a carriage assembly of the second portion using an engaging surface and a complementary engaging surface. In yet another aspect, a carriage assembly of the first portion is engaged to a carriage assembly of the second portion when a shape memory alloy element is activated. In yet another aspect, a carriage assembly of the first portion is engaged to a carriage assembly of the second portion using a pin and a slot. In yet another aspect, a carriage assembly of the first portion is engaged to a carriage assembly of the second portion using a mechanical connector. In yet another aspect, a carriage assembly of the first portion is engaged to a carriage assembly of the second portion using a magnetic field.

In another aspect, the force generator produces rotational energy. In another aspect, the force generator comprises a motor. In another aspect, force generator comprises a pump. In another aspect, the application of force to the force transmission element in the first portion moves the carriage assembly in the first portion relative to the at least one guideway in the first portion. In another aspect, the application of force to the force transmission element in the first portion moves the articulating instrument. In another aspect, the articulating instrument is a medical instrument. In another aspect, the medical instrument is a segmented endoscope. In another aspect, the force transmission element of the second portion is connected to at least one segment of a segmented endoscope.

In another aspect, the connection assembly includes a sensor that indicates an operational condition of the connection assembly. In one aspect, the connection assembly comprises a quick release mechanism. In another aspect, the connection assembly comprises a mechanical interface adapted to transfer force from the first portion to the second portion. In another aspect, a guideway defines a limited range of travel for a carriage assembly. In yet another aspect, a guideway comprises a stop to limit carriage assembly movement. In another aspect, a guideway comprises a protrusion. In another aspect, the protrusion is adapted to retain a carriage assembly. In another aspect, the guideway comprises a recess. In yet another aspect, the recess is adapted to retain a carriage assembly.

In another aspect of the invention, there is provided a system for controlling the movement of an articulating instrument. The system includes a connection assembly having a first portion removably coupled to a second portion. The first portion comprising a carriage assembly connected to a first force transmission element. The second portion comprising a carriage assembly connected to a second force transmission element. An actuator is coupled to the first force transmission element. An articulating instrument is coupled to the second force transmission element. A control system responsive to inputs for controlling movement of the articulating instrument.

In one aspect, the control system controls the articulating instrument movement by regulating the operation of the actuator. In another aspect, the first portion carriage assembly is engaged with the second portion carriage assembly when the first portion is coupled to the second portion. In yet another aspect, the first portion carriage assembly is mechanically engaged with the second portion carriage assembly. In yet another aspect, the first portion carriage assembly is magnetically engaged with the second portion carriage assembly. In yet another aspect, the first portion carriage assembly is pneumatically engaged with the second portion carriage assembly. In yet another aspect, the first portion carriage assembly engaged with the second portion carriage assembly using suction or vacuum. In yet another aspect, the first portion carriage assembly is hydraulically engaged with the second portion carriage assembly.

In yet another aspect of the invention, the first portion carriage assembly is engaged with the second portion carriage assembly using a set of engaging teeth. In another aspect of the invention, the first portion carriage assembly is engaged with the second portion carriage assembly using a set of engaging gear teeth. In another aspect of the invention, the first portion carriage assembly is engaged with the second portion carriage assembly using a spur gear. In another aspect of the invention, the first portion carriage assembly is engaged with the second portion carriage assembly by activating a shape memory alloy element. In another aspect of the invention, the first portion carriage assembly is engaged with the second portion carriage assembly using at least one hook. In another aspect of the invention, the first portion carriage assembly is engaged with the second portion carriage assembly using a threaded member. In another aspect of the invention, the first portion carriage assembly is engaged with the second portion carriage assembly by engaging a slot and a pin. In another aspect of the invention, the first portion carriage assembly is engaged with the second portion carriage assembly using a spline and a rack. In another aspect, the first portion carriage assembly is engaged with the second portion carriage assembly using a rack; a pinion; a spur gear; a worm gear, or combinations thereof. In another aspect, the first portion carriage assembly is engaged with the second portion carriage assembly using an electromagnet and/or permanent magnet or other magnetic forces.

In one aspect of the invention, the first force transmission element or the second force transmission element is a cable. In another aspect of the invention, the first force transmission element or the second force transmission element is a piston. In one aspect of the invention, the first force transmission element or the second force transmission element is a Bowden cable.

In one aspect of the invention, the actuator is a motor. In one aspect of the invention, the actuator is a pump. In another aspect of the invention, the actuator is a vacuum pump. In one aspect of the invention; the actuator is a pneumatic pump.

In another embodiment of the present invention, the first portion carriage assembly is disengaged with the second portion carriage assembly when the first portion is disengaged from the second portion.

In one embodiment of the present invention, there is provided a system for controlling the movement of an articulating instrument and the articulating instrument is a medical instrument. In another aspect of the invention, the medical instrument is a segmented endoscope. In another aspect of the invention, the first portion is coupled to the second portion and movement of the first force transmission element moves a segment of the segmented endoscope. In another aspect of the invention, a control system generates a command to operate the actuator and thereby move a segment of the segmented endoscope in response to an input.

In one aspect of the invention, the input is provided by a user. In another aspect of the invention, the input is provided by a surgical planning program. In another aspect of the invention, the input is provided by an image of the desired path of travel for the segmented endoscope.

In another aspect of the present invention, there is provided a connector for coupling a force to move a segmented medical instrument having a connector having a first connector housing releaseably coupled to a second connector housing. The first connector housing having a plurality of guideways and a carriage assembly disposed in each guideway. The carriage assembly is adapted to be coupled to a force generator. A second connector housing having a plurality of guideways and a carriage assembly disposed in each guideway. A force transmission element attached to each carriage assembly and adapted for connection to a segmented medical instrument. In one aspect of the present invention, a carriage assembly in the first connector housing is adapted to be coupled to the force generator using a force transmission element. In one aspect, a force transmission element attached to a carriage assembly in the second connector housing passes through a proximal segment of the segmented medical instrument and is attached to a distal segment of the segmented medical instrument. In another aspect of the invention, application of a force to a carriage assembly in the first connector housing moves a carriage assembly in the second connector housing. In another aspect, application of a force to a carriage assembly in the first connector housing moves a segment of the segmented medical instrument. In one aspect the carriage assembly in the second connector housing moves along a guideway. In another aspect, at least one of the first connector housing and the second connector housing comprising a slack area. In another aspect, the slack area is in the first connector housing and a portion of the slack area is in a non-linear orientation to the guideways in the first connector housing. In another aspect, the slack area is in the second connector housing and a portion of the slack area is in a non-linear orientation to the guideways in the second connector housing. In yet another aspect, the slack area contains the force transmission element coupled to the first connector housing arranged in an angular relationship to the guideways in the first connector housing. In yet another aspect, the slack area contains the force transmission elements of the second connector housing arranged in an angular relationship to the guideways in the second connector housing.

In another aspect of the present invention, there is provided a connector having a sensor to detect an operational characteristic of the connector. In one aspect, the operational characteristic of the connector is the engagement of a carriage assembly in the first connector housing to a carriage assembly in the second connector housing. In another aspect, the operational characteristic of the connector is the disengagement of a carriage assembly in the first connector housing to a carriage assembly in the second connector housing. In another aspect, the operational characteristic of the connector relates to the operational condition or performance of the connector such as friction losses, wear, component-degradation and the like. In another aspect, the operational characteristic of the connector is the tension in a force transmission element. In another aspect, the operational characteristic of the connector is the torque exerted on a force transmission element. In another aspect, the operational characteristic of the connector is a force acting on a force transmission element. In another aspect, the operational characteristic of the connector is a force acting on a carriage assembly. In another aspect, the characteristic of the connector is the range of travel of a carriage assembly. In another aspect, the connector includes an indicator that provides information about the segmented medical instrument coupled to the connector. In one aspect, the information is related to the time since maintenance was performed on the segmented medical instrument. In another aspect, the information is related to the physical parameters of the segmented medical instrument. In another aspect, the information provided by the indicator alters the manner in which the segmented medical instrument is actuated. In another aspect, the segmented medical instrument is an endoscope.

BRIEF DESCRIPTION OF THE DRAWINGS

FIGS. 5A and 5B illustrate a manner of engagement between the first and second connector portions.

FIGS. 7A and 7B illustrate alternative carriage assembly embodiments.

FIGS. 9B and 9C shows a second variation of a quick-release mechanism for attaching and detaching the tendon driven endoscope from the actuators that relies on a nail-head configuration to actuate the tendons.

FIG. 19 illustrates an exemplary embodiment of an actuator engaged with a force transmission element.

FIGS. 20A and 20B illustrate another exemplary embodiment of an engagement system to engage a connector portion.

FIG. 21 illustrates an exemplary embodiment of a pair of force transmission elements.

FIGS. 31A, 31B and 31C illustrate an exemplary embodiment of a complementary engagement pair including a saw tooth male member and correspondingly shaped saw tooth female receiver.

DETAILED DESCRIPTION OF THE INVENTION

Figure 1:
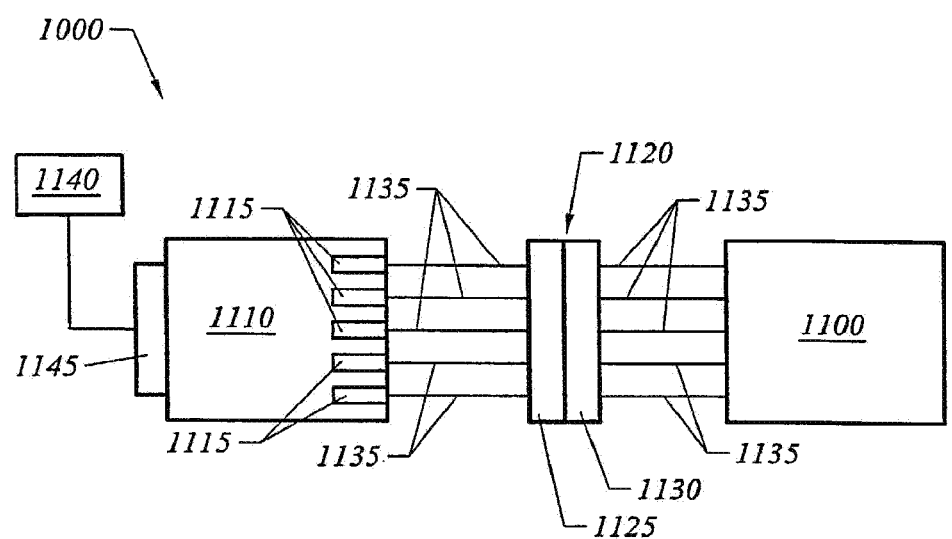
FIG. 1 shows a schematic view of a system for articulating a controllable article.

FIG. 1 illustrates a schematic view of a system 1000 for moving a controllable article 1100. A force generator under control of one or both of a user input device 1140 and a system controller 1145 generates forces that are used to move the controllable article 1100. The forces generated by the force generator are transmitted to the controllable article using force connecting elements 1135 and a connector assembly 1120. The controllable article may also be an articulating instrument.

A connector assembly 1120 completes the transmission of power generated by the force generator 1110 and applied to the controllable article 1100. The two portions 1125, 1130 of the connector assembly 1120 are disengagably coupled. The connector portion 1125 is the first connector portion or the force generation side connector. The connector 1130 is the second connector portion or the controllable article side connector portion. When the connector portions 1125, 1130 are in a coupled condition, the force transmission elements 1135 are joined and force generated by the force generator 1110 is applied to the controllable article 1100. When the connector portions 1125, 1130 are not coupled, the connector portion 1130, force transmission elements 1135 and the controllable article 1100 may be removed, in some embodiments as a single integrated unit, from the connector portion 1125, force transmission elements 1135 and the force generator 1110 or actuators 1115.

The connector assembly 1120 represents one advantage of the present invention. The ability to quickly connect and disconnect the two portions 1125, 1130 allow a single force transmission portion to be used with multiple controllable articles. Currently, articulating instruments such as, for example, endoscopes typically have only 4 cables to provide limited control at the tip of the endoscope. The present invention may be advantageously utilized by existing articulating instruments to allow endoscopes with only a few force transmission elements to be quickly and more readily connected to a force generator. Moreover, connector embodiments of the present invention provide compact organization and efficient coupling of numerous force transmission elements used by highly maneuverable controllable articles. As the degree of control exerted over controllable articles increases, the number of force transmission elements needed to exert that control also increases. Increasing numbers of force transmission elements drive the need for connector solutions such as those presented by embodiments of the present invention that afford a highly compact and organized coupling arrangement of the force transmission elements.

One advantage of the simplified connection/disconnection aspect of the present invention, is that in many instances it may be desirable to have the controllable article easily separable from the actuators, force generators or controllers for cleaning, disinfecting or maintenance. The quick-release characteristic of the connectors of the present invention enable an efficient way to achieve a controllable article that is easily removable, replaceable or interchangeable. In this manner, a single controller and actuator system may be used to articulate multiple controllable instruments. After one instrument is released, another is quickly and easily connected and ready for service.

Another advantage of the connectors of the present invention is that the proximal ends of the force transmission elements attached to the controllable article can be organized to allow predictable attachment point to the corresponding force transmission elements coupled to the actuators. The plurality of force transmission elements may be organized into a bundle, array, or rack. Such organization provides a known attachment point between the force transmission elements of the actuators to the force transmission elements of the articulating instrument. Additionally, as will be seen in the examples that follow, dozens of force transmission elements will be utilized in advanced articulating instruments. Embodiments of the connectors of the present invention provide a scaleable solutions that allows a user, in a single motion, to connect all the force transmission elements coupled to the actuators to those coupled to the controllable article. Moreover, the single action connection feature of some embodiments of the present invention also provides an important safely feature if an unsafe condition arises, the actuators or force generators may be quickly disconnected from the articulating instrument.

As will be detailed below, this organization could also provide other advantages to the controllable article, such as allowing active or passive control of the tendon slack. Furthermore, the proximal ends of each tendon can be modified to allow attachment and manipulation, e.g., the ends of the tendons may be held in a specially configured sheath or casing.

Additionally, the connector 1120 may include sensors and/or safety features to help ensure proper operation and articulation of the controllable article. In the discussion that follows, the connector refers to embodiments of the connector 1120 as well as embodiments of the first and second connector portions 1125, 1130. One sensor or feature may indicate or detect translation or movement of the engaging elements (i.e., carriage assemblies 120 described below) or the force transmission elements 1135 themselves. Another sensor or feature may also detect and measure or otherwise quantify the amount of translation or movement of the engaging elements (i.e., carriage assemblies 120 described below) or the force transmission elements 1135 themselves. Another sensor may be utilized to indicate proper engagement of either the connector portions 1125, 1130 or each of the individual engaging elements (i.e., carriage assemblies 120). Another sensor or indicator may be used to generate a signal based on contacting a limit stop or the length of travel of a particular component. Another sensor may be used to detect component failure within the connector 1120.

Returning to FIG. 1, the system includes a force generator 1110. The force generator may be any conventional generator used to provide or generate sufficient force to the movement of the controllable article 1100. The force generator may provide, for example, mechanical force, hydraulic force, rotational force, or pneumatic force. Force generators may also utilize shape memory alloys (SMA) and/or electroactive polymers (EAP). Optionally, and illustrated in the embodiment of FIG. 1, the force generator 1110 may itself be an actuator or include a plurality of individual actuators 1115 acting as individually controllable force generators for each force transmission element 1135. Alternatively, an individual actuator 1115 may be connected to drive and control a subset of the total number of elements 1135 but more than one element. For example, an individual actuator may be connected to drive two, three, four or more individual force transmission elements. A plurality of first force transmission elements 1135 are illustrated having a first end connected to a force generator 1110; 1115 and a second end having a first connecting element within the connector portion 1125. Details of several illustrative connecting element embodiments are described in detail below.

The controllable article 1100 is connected to the connector portion 1130 by a plurality of force transmission elements 1135. The controllable article may be any of a number of commercial, industrial or medical devices. These force transmission elements have a first end connected to the controllable elements, modules or components within the controllable article. The controllable article may be, for example, a robotic handler having a number of articulating linkages. In this example, the force transmission elements 1135 attached to the connector 1130 are connected to transmit force to the articulating linkages. In another illustrative embodiment, the controllable article may be a segmented, articulating instrument. In this case, the force transmission elements 1135 attached to the connector 1130 will also be connected so as to transmit force to the individual segments to articulate the instrument. The ends of the force transmission elements 1135 within the connector 1120 are adapted to engage one another when the connector portions 1125, 1130 are coupled. In some embodiments, the first and the second elements are mechanically coupled. Other types of coupling configurations are possible and are described in greater detail below.

A controllable article 1100 includes at least one segment or module, and preferably several segments or modules, which are controllable via a computer and/or electronic controller (controller) 1140 located at a distance from the controllable article 1100. Each of the segments has force transmission elements 1135, tendons, mechanical linkages or elements connected to a force generator 1110 or an actuator 1115 to allow for the controlled motion of the segments or modules. The actuators driving the tendons (as a specific example of a force transmission element 1135) may include a variety of different types of mechanisms capable of applying a force to a tendon, e.g., electromechanical motors, pneumatic and hydraulic cylinders, pneumatic and hydraulic motors, solenoids, shape memory alloy wires, electroactive polymer actuated devices, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, heat, etc., to each of the bundles to actuate a linear motion in the wire bundles which in turn actuate the tendon movement. The linear translation of the actuators within the controller is configured and scaled in conformity with the desired movement of the controllable article and may vary depending upon application of the controllable article. Some commercial applications may include controllable articles articulating in large movements measured in feet. Still other applications, such as for example, medical applications, may find that the controllable article is configured for tighter control to enable more precise movement over a relatively short distance, e.g., within a few inches or less such as ±1 inch, to accomplish effective articulation depending upon the desired degree of segment movement and articulation.

In one specific embodiment, the force generator is a motor. The motor is coupled to a leadscrew assembly, so that when the motor rotates, it transmits torque to the leadscrew. A modified nut on the leadscrew is constrained to prevent rotational motion, so that when the leadscrew is rotated, the nut is translated along the axis of the leadscrew. The torque from the motor is thereby translated into linear motion. In this specific embodiment, the force transmission element is a cable that is connected to the nut on one end and a carriage assembly 120 on the other end. The linear motion of the nut translates into force on the cable. As such, the leadscrew movement is translated into linear movement of a carriage assembly in one connector hence to another carriage assembly in another connector assembly connected to the controllable article. In one specific embodiment, 64 of the leadscrew assemblies are arranged in modules for easy organization and maintenance. The modules are supported in a chassis that also houses the first portion of the connector described above. More or fewer leadscrew assemblies may be used depending upon application.

Figure 2:
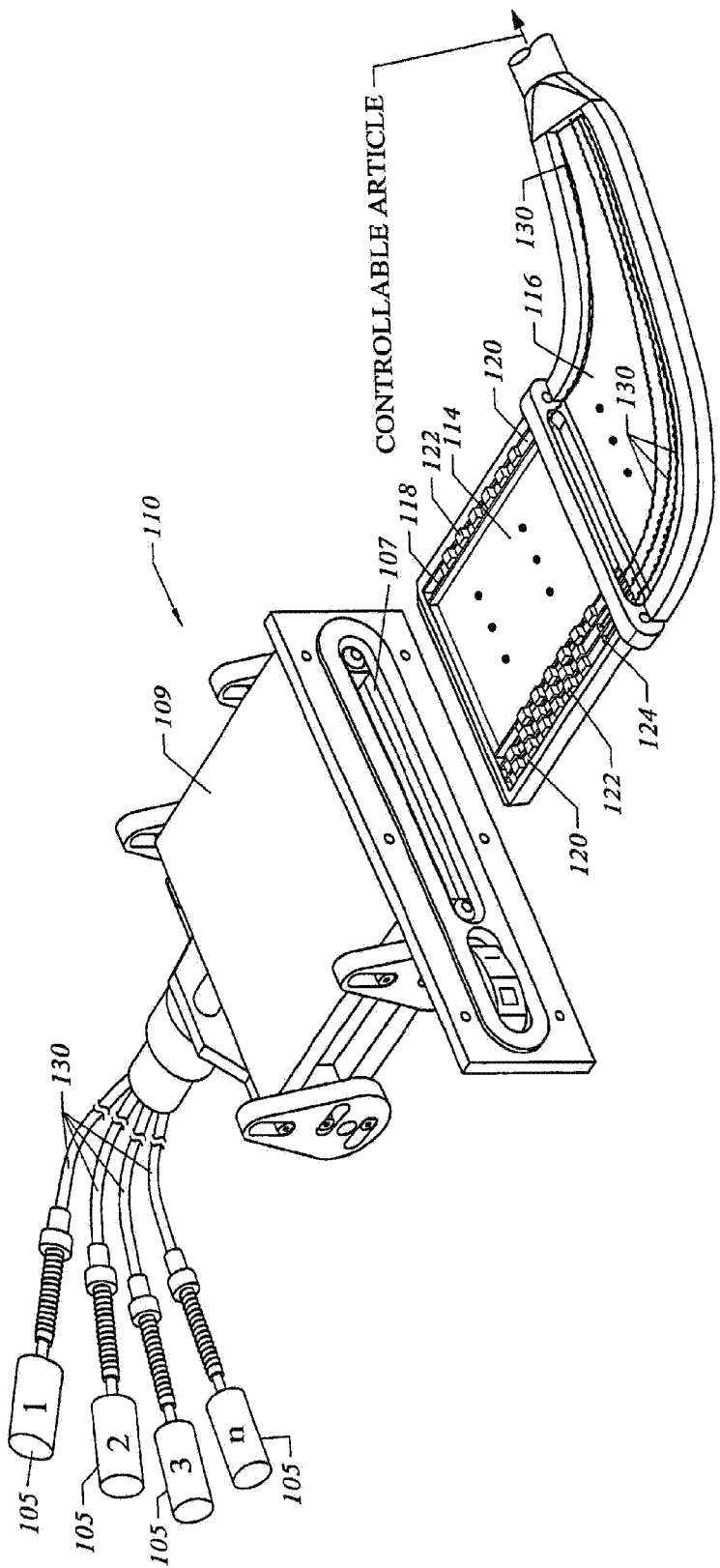
FIG. 2 is a perspective view of one embodiment of the connector assembly.

FIG. 2 illustrates a perspective view of a connector assembly 110 according to one embodiment of the present invention. The connector assembly 110 includes a first connector portion 112 (not shown but within housing 109) and a second connector portion 114. The first connector portion 112 is within the housing 109. The second connector assembly 114 includes a plurality of guideways 118 each containing a carriage assembly 120. Each carriage assembly contains one or more than one engaging feature 122. Engaging features 122 on carriage assemblies 120 in the second connector portion 114 are adapted to engage with the engaging features 122 on carriage assemblies 120 of the first connector portion 112 (see FIG. 3). One end of the carriage assemblies are connected to force transmission elements or cables 130. In the illustrated embodiment, the cables are Bowden cables. The cables run through a slack area 116. The slack area 116 allows added space for cable slack that may build up during controllable article movement. Thereafter, the cables are connected as desired to the controllable article.

The housing 109 provides a structural base for supporting the connector assembly 110. In this embodiment, the first connector portion 112 (not shown) is secured within the housing 109. The first connector portion and its carriage assemblies are connected via force transmission elements 130 to actuators 105. While four actuators 105 are illustrated, it is to be appreciated that more actuators may be used to drive a corresponding number of carriage assemblies. The housing 109 also provides a opening 107 configured to receive the second connector portion 114. Optionally, either one or both of the opening 107 or a portion of the second connector portion 114 may be keyed to ensure correct orientation prior to connection. When the second connector portion 114 is placed within the opening 107, the first and second connector portions 112, 114 are brought into engagement using an appropriate quick release mechanism, such as for example a cam actuated lever or other engagement device as known to those of ordinary skill in the art. When the first and second connector portion 112, 114 are engaged, forces generated by actuators 105 are transmitted to the controllable article. In one embodiment, relative movement between the first connector portion and the second connector portion is used to couple the first connector portion to the second connector portion. In one embodiment, nearly vertical movement between the first connector portion and the second connector portion is used to engage the first and second connector portions. In another embodiment, the coupling force between the first and second connection portions acts nearly orthogonal to the direction of movement of the individual connection elements (i.e., carriage assemblies 120) within the first and second connection portions.

The connector 110 embodiment of FIG. 2 and other embodiments of the present invention may also provide a number of safety features. For example, the forces used to bring together and hold the carriage assemblies of the first and second connector portions in locking cooperation may be set to such a level that ensures these is positive engagement and no slip. The force holding the connector portions could be set to separate at a force below a threshold force that could damage a component in the force transmission pathway, such as for example, a force transmission element. Alternatively, carriage assemblies could be attached to their force transmission elements at some margin of safety whereby in the event an actuator loses control, the respective carriage assembly would separate from its force transmission element.

Figure 3:
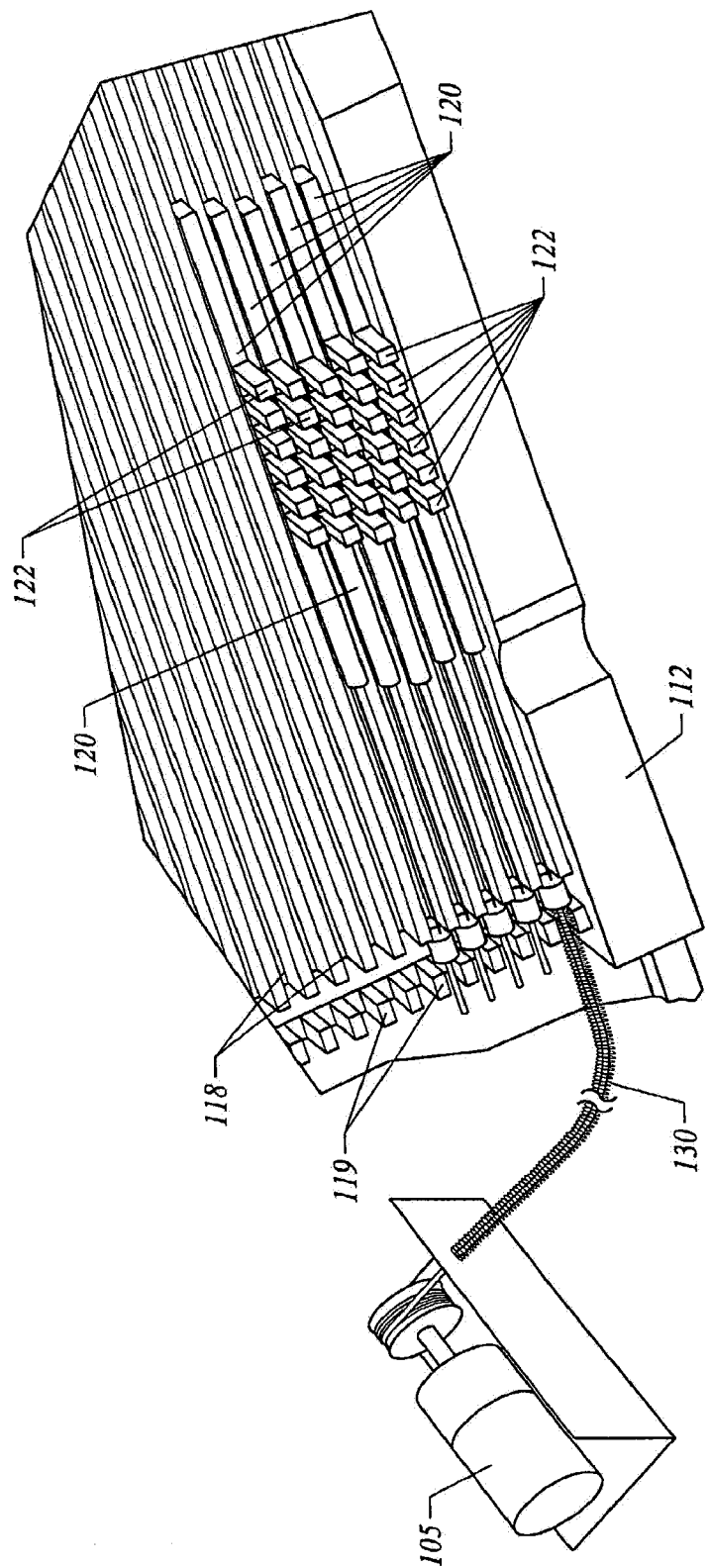
FIG. 3 shows a detailed perspective view of one variation for a carriage assembly.

FIG. 3 shows an embodiment of the first connection portion 112 coupled to an actuator 105. The first connector portion 112 is constructed similar to the second connector portion 114 described above. As such, the first connector portion 112 includes a plurality of guideways 118 and carriage assemblies 120. Instead of connecting to the controllable article, the carriage assemblies 120 of the first connector portion 112 are appropriately connected to actuators 105.

Figure 4:
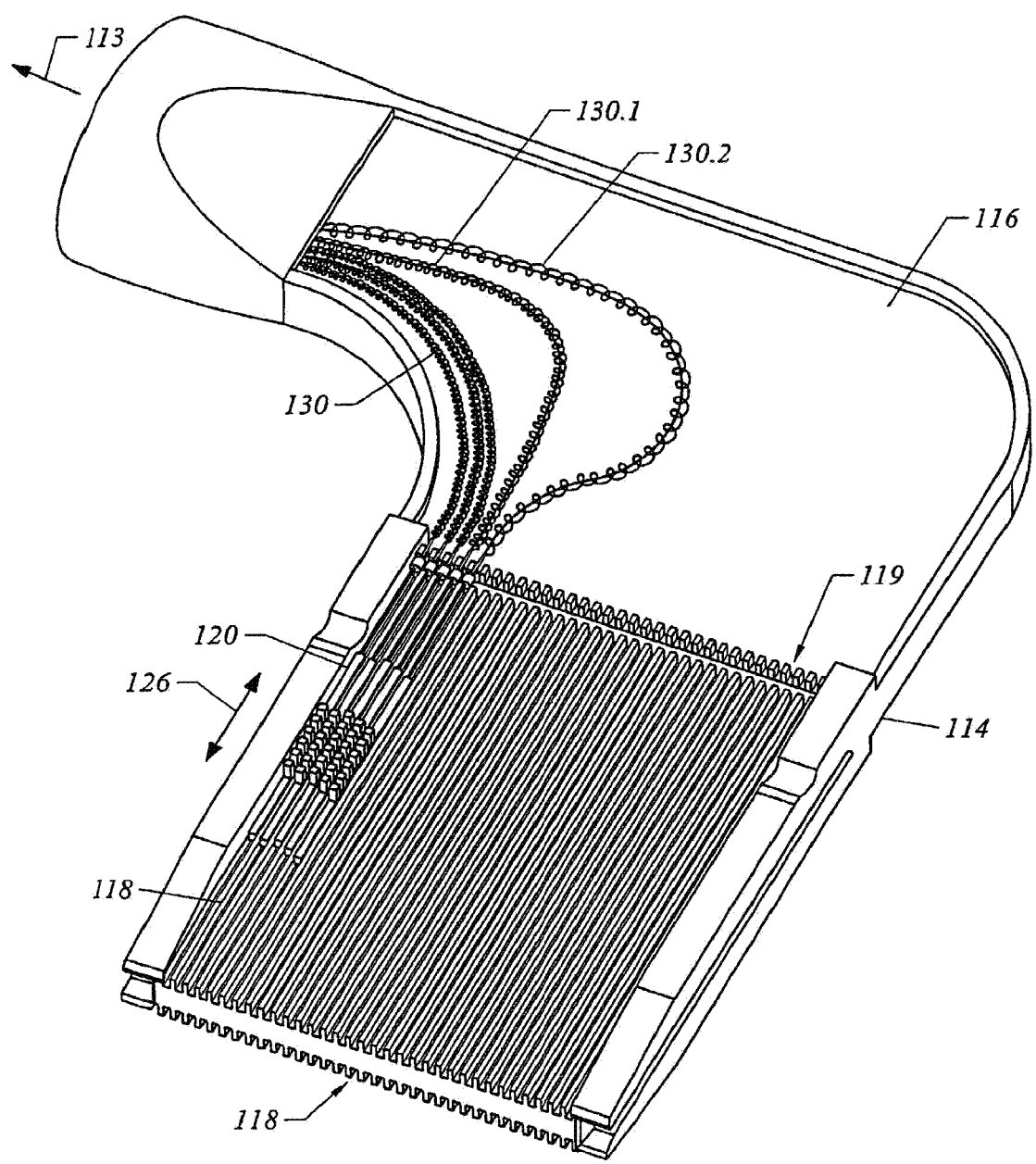
FIG. 4 shows a variation of a connector portion having a slack area.

FIG. 4 shows a perspective view of one embodiment of the second connector portion 114. The second connector portion 114 organizes and houses the carriage assemblies 120 within guideways 118. By connecting the force transmission elements to the carriage assemblies, this organization is provided to the plurality of force transmission elements needed in highly controlled articulating instruments and controllable articles. In the illustrated embodiment, the second connector portion provides 64 guideways with 32 guideways in the upper face 114A and 32 guideways in the lower face 114B (the edge of the guideways 118 of the lower face 114E are visible). The embodiment of FIG. 4 illustrates the compact nature of connectors according to the present invention. Because of the highly efficient space utilization, a connector of the present invention may provide articulation force to 64 separate cables in a space only slightly larger than the width of 32 cables or one-half the total number of cables. Alternatively, the width of the connector is only slightly larger than the width of a single carriage assembly multiplied by one-half the number of force transmission elements.

It is to be appreciated that both double and single sided connector portions are possible. For example, the double-sided second connector portion may be coupled to two single sided first connector portions (i.e., one single sided first connector engages with the second connector upper face and the other engages with the lower face, for example FIG. 203.) Many different connector shapes and configurations are possible. For example, in another alternative configuration, two double-sided second connectors 114 may be engaged by one double sided first connector portion 112 between the double sided second connectors 114 and a first single sided first connector above one and a second single sided first connector below the other second connector portion 114. In each of these alternatives, the mechanical workings within the housing 109 provide proper alignment and quick disconnect between the various connector portions regardless of the numbers used.

The connectors and housing 109 may be formed from any suitable material having sufficient strength to transmit the forces or energy used. Suitable materials include metals, plastics, extrusions, injection molded parts, forged, and/or metal injection molded parts, In addition, the bearing surfaces may be coated with suitable low friction coatings to reduce friction losses within the connectors such as between the carriage assemblies and the guideways. One or more surfaces within the connector assembly may be coated as desired. Suitable coatings include, for example, Teflon, PTFE, and other low friction coatings. In addition, the bearing surfaces may include a viscous coating or include other bearing structure or surfaces such as, for example, ball bearings, linear bearings, or air bearings and the like.

Connector assembly portion 114 has a plurality of guideways 118 for organizing the array of tensioning members and/or cables 121 used to control a controllable article, Guideway 118 may be a U-shaped channel formed integrally within housing 114 as illustrated or it may be manufactured separately and attached onto housing 114. As described in greater detail below with regard to FIGS. 8A-8D, embodiments of the guideway 118 may comprise tracks or rails aligned adjacent to each other. In some embodiments, each of the rails may form a protrusion extending along the length of guideway 118 such that a rectangularly shaped-rail is formed. The rail or track may be of any shape such as, for example, rectangular, concave, convex, rounded or curvilinear. A complementary shape is formed in the engaging face of the carriage assembly for that guideway. The number of rails may correspond to the number of tensioning members utilized for a controllable device or more rails may be provided to accommodate for additional tensioning members. In some embodiments, the rails align parallel to one another although in other variations, the shape and alignment of the rails may be varied.

As illustrated in FIGS. 3 and 4, connected to at least one of the tensioning members and/or cables 121 are cable carriage assemblies 120. There may be one or several carriage assemblies 120 configured to traverse along the guideway 118. As in these illustrative examples, each carriage assembly 120 may be secured to a cable 121 extending from a tensioning member or force transmission element. As best seen in FIG. 3, the cable 121 passes through the cable stop 117, the coil tube 111 and is suitably coupled to the actuator 105. In the illustrative embodiment of FIG. 3, the cable 121 is wrapped about the end of the actuator 105. The cable stop 117 is anchored in the gap between the frame stop 119 and the end of the guideway 118. The ends of the coil tube 111 are anchored between the actuator frame or a support 115 and the cable stop 117. Similar to a conventional Bowden cable arrangement, the above described anchoring configuration retains the coil tube 111 in compression while the cable 121 remains in tension and transmits force from the actuator 105. As best illustrated in FIG. 4, the carriage assembly 120 is moved within the guideway 118 as indicated by the direction of travel 126. A force transmission element (i.e., 130, 130.1, 130.2) attached to a carriage assembly 120 and the controllable article 1100 transfers that motion 126 to move the controllable article 1100 accordingly. The number of carriage assemblies 120 utilized will vary depending upon the number of tensioning members utilized for articulation of the controllable article.

Guideway 118 may be configured to provide a limited range of travel for the translational movement of cable carriage assemblies 120. For instance, guideway 118 may have a frame stop 119 defined at one end of the guideway 118 so that carriage assemblies 120 may be securely seated and aligned with each rail. Frame stop 119 may define a portion of the guideway that is discontinuous such that a carriage assembly 120 may be seated within the discontinuity. Although the discontinuity is shown in FIG. 4 at one end of the guideway 118, it may alternatively be positioned at the other end of in another location along the guideway 118. Alternatively, frame stop 119 may define a crimp, clamp, adhesive, mechanical fastener, or some other method as known in the art for securing to prevent the excess movement of carriage assembly 120.

In the illustrated embodiment of the second connector portion 114, the second connector portion 114 includes a cable passageway or slack area 116. Slack area 116 is an area sufficiently spacious to allow for the inclusion of slack in the tendons and/or cables which may be routed through and/or bend within the passageway 116, as described in further detail below. The passageway 116 may be curved such that controllable article interface 113 and guideway 118 are angled relative to one another, such as the illustrated angle of about 90° but may range between 0° to 180°. The slack area angle is measured between a line representing the direction of movement of the carriage assembles—i.e., direction of travel 126—and a line directed towards the articulating instrument through interface 113. The size and exact configuration of the slack area, if included, will depend upon the number size, shape and flexibility of the force transmission elements used in a particular application. As such, the slack area may have any of a wide variety of shapes or curvature to provide an accommodation for the excess or slack cable length temporarily created during movement or manipulation of the controllable article.

In the illustrated embodiment of FIG. 4, the force transmission elements 130, 130.1 and 130.2 are Bowden cables (i.e., cable 121 within a flexible housing or coil tube 111). As the controllable article is manipulated by movement of the cables, the cable housings for the cables may be moved longitudinally proximally and/or distally as well. The slack area 116 is shaped and sized to accommodate a number of tensioning elements in the connector assembly. The slack area 116 may simply be a compartment sufficiently large enough to provide space for the cables 130, 130.1, and 130.2, for example, to extend in an expanded configuration, to allow for cable slack in the connector 110. The force transmission elements 130, 130.1, and 130.2 illustrate the relative amount of space required for coil tube and cable extension. Illustrated are various degrees of extension from low extension in force transmission element 130 to moderate and high degrees of extension in force transmission elements 130.1 and 130.2 respectively. Where a slack area 116 is utilized, the relationship between the connector assembly portion and the slack area need not be angled, as illustrated, but may instead provide for a collinear arrangement.

Figure 5B:
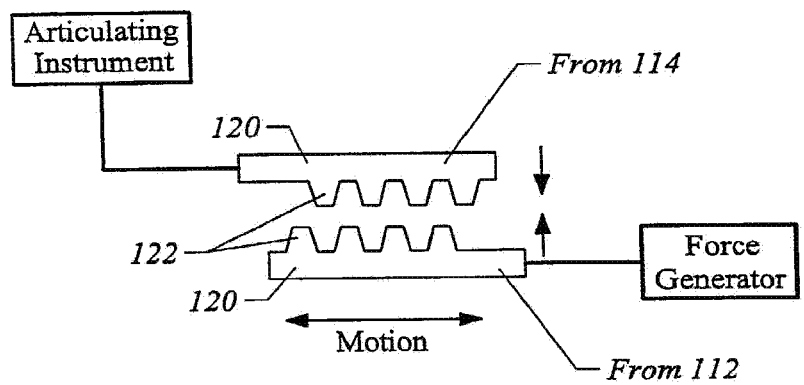

FIGS. 5A and 5B illustrate one manner of engagement between the carriage assemblies 120 of the connector portions 114, 112. When the two connector portions are brought together, the carriage assemblies 120 arranged on one side of a double sided first connector portion 112 align with and engage the carriage assemblies 120 arranged on one side of a double sided second connector portion 114 (FIG. 5A). One possible engagement between the features 122 of the carriage assemblies 120 is illustrated in FIG. 5B as the carriage assemblies are moved in the direction of the arrows. While FIG. 5B illustrates both connectors 112, 114 moving together to join one face, it is to be appreciated that the connectors may engage through relative movement in another direction (i.e., lateral or circular movement, for example) and that one connector may remain fixed while the other moves to engage and that, when engaged, the connectors engage on more than one face (i.e., FIGS. 20A and 20B).

Figure 6:
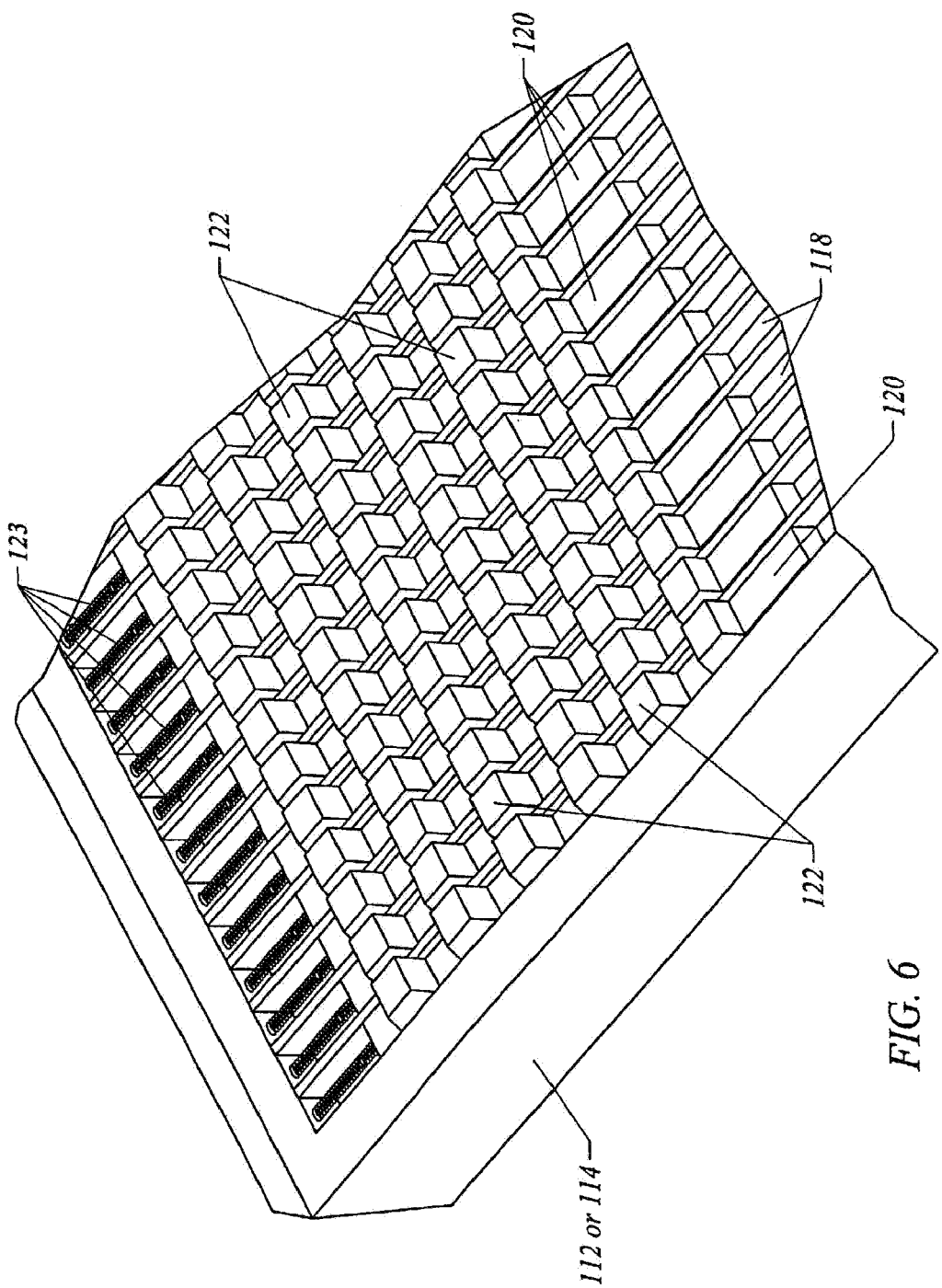
FIG. 6 illustrates carriage assemblies having positioning elements.

One potential problem when engaging connector portions 112, 114 is the proper alignment of the carriage assemblies prior to engagement. Any number of mechanical alignment features and techniques may be used to align the carriage assemblies into a zero or alignment position prior to engagement between a first and a second connector portion. FIG. 6 illustrates one embodiment where carriage assembly alignment is provided by placing an alignment element 123 adjacent a carriage assembly. In this manner, each carriage assembly is urged into a similar position within a guideway 118. In the illustrated embodiment, the alignment element may be a bias element such as spring. Alternatively, a small alignment feature may be provided in each guideway to temporarily engage a carriage assembly. The initial application of force applied to the connector after engagement is used to move the carriage assemblies off the alignment feature in preparation for articulating the controllable article. In one embodiment, each connector portion 112, 114 includes an alignment feature that urges the carriage assembly into an alignment position. An alignment position is a position of a carriage assembly in a guideway of one connector portion to further the engagement of that carriage assembly to a similarly positioned carriage assembly on the other connector portion.

FIGS. 7A and 7B show detailed perspective views of two alternative carriage assembly embodiments 120' and 120". Carriage assemblies 120', 120" provide a rack 130 configured to correspondingly fit and slide along a rail disposed within or other feature configured within a guideway 118. In the illustrated embodiments, rack 130 defines a U-shaped or generally rectangular channel 132.

FIG. 7A illustrates an embodiment of a rack 130 having a channel 132. One end of a force transmission cable 144 is crimped 138 or otherwise fastened with adhesive, soldered, etc. to the rack 130. The cable 144 extends through stop 146 and through coil tube 142. Cable 144 may extend beyond stop 146 and the other end connected, for example, to a force generator or to an articulating segment of an articulating instrument. A coil tube 142 may optionally extend beyond assembly stop 146 to provide support between the cable 144 and stop 146 interface to aid in preventing cable 144 from kinking. Once the rack 130 is placed within an appropriately configured guideway 118 (i.e., one having a complementary shaped rail or feature to engage channel 132), the stop 146 is held within assembly stop 119 in connector assembly first portion 112 or second portion 114.

FIG. 7B illustrates an embodiment utilizing a telescoping tube 140, 136. Inner tube 136 extends within the interior of telescoping tube 140 in a slideable arrangement. Inner tube 136 may be attached within channel 132 at crimps 138 or, alternatively, to the rack 130 with adhesive, solder or other fastening techniques known in the art. One end of telescoping tube 140 may terminate in stop 146, which may be positioned within or adjacent to frame stop 119. Extending from assembly stop 146 is cable 144, which may further extend and be connected to a force generator or a portion of an articulating instrument. Alternatively, cable 144 may further extend from assembly stop 146 directly into a segment of an articulating endoscope. A coil tube 142 may extend partially beyond assembly stop 146 to provide support between the cable 144 and stop 146 interface to aid in preventing cable 144 from kinking or to conventionally assist in the transmission of force. Optionally, one end of cable 144 may be secured to the distal end of inner tubing 136 or cable 144 may be disposed through inner tubing 136 and extend towards the proximal end of inner tubing 136 for direct attachment to rack 130 using a crimp 138. During operation as carriage assembly 120" is translated, rack 130 rides along a rail in guideway 118 while inner tubing 136 slides through telescoping tube 140 relative to the stationary assembly stop 146. The distal and/or proximal movement of rack 130 will likewise urge cable 144 to move in accordance with rack 130, thereby transferring the longitudinal motion either directly or indirectly to the articulating instrument segment or portion attached to the cable 144.

Also shown in FIG. 7B is an interface portion 134 upon at least one of the outer surfaces of rack 130 to provide for a secure engagement interface with an actuator, e.g., electric motor, shape-memory alloy actuator, hydraulic or pneumatic actuator, etc. Interface portion 134 may be formed into a series of gear-shaped ridges, as shown, to provide engagement surfaces against a corresponding member attached to the actuator; alternatively, interface portion 134 may be configured to have a receiving clamp or slotted interface to provide for engagement or any other type of engagement interface as known in the art.

Although the embodiments of FIGS. 7A and 7B illustrate a rectangular or generally U-shaped channel 132, other configurations of the channel and corresponding rail are possible. The sliding channel 132 may also be formed in a variety of open shapes, such as semi-spherical, semi-elliptical, etc., provided the rail upon which rack 130 moves upon is formed in a corresponding shape. Examples of alternative rail and channel configurations are illustrated in FIGS. 8A-8D.

Figure 8A:
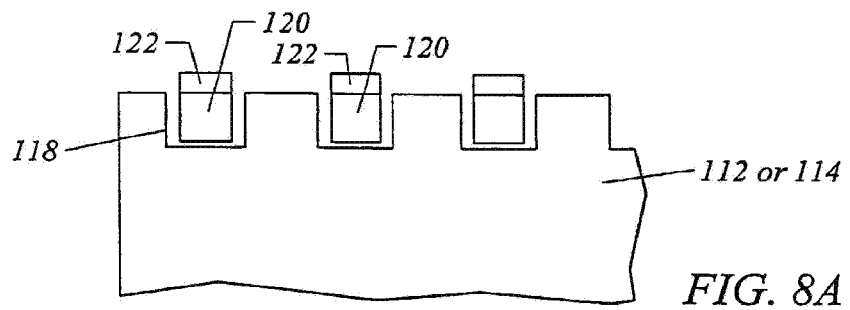
FIGS. 8A, 8B, 8C and 8D illustrate various exemplary embodiments of carriage assemblies and guideways.

FIGS. 8A-8D illustrate alternative guideway and carriage assembly arrangements. Note that the carriage assembly/guideway arrangements described are applicable to either or both of the full and second connector assemblies 112, 114. FIG. 8A illustrates the carriage assembly 120 guideway 118 arrangement of FIGS. 3, 4 and 5A. The carriage assembly 120 shape is accommodated by the shape of guideway 118.

Figure 8B:
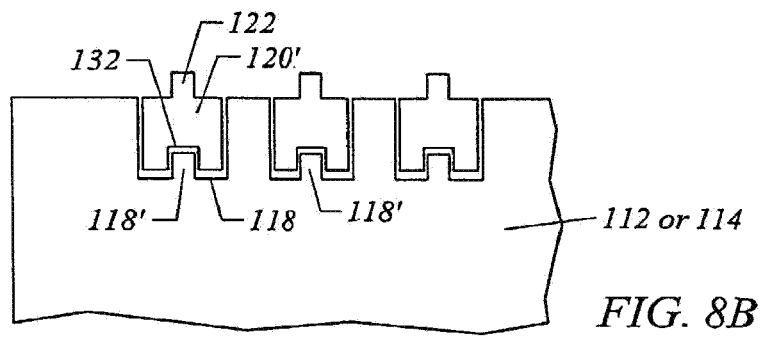
Figure 8C:
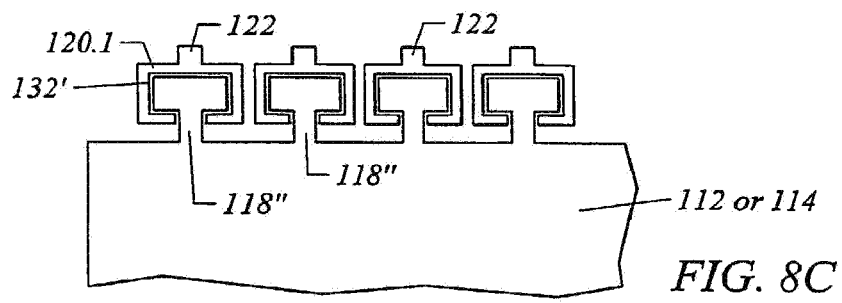
Figure 8D:
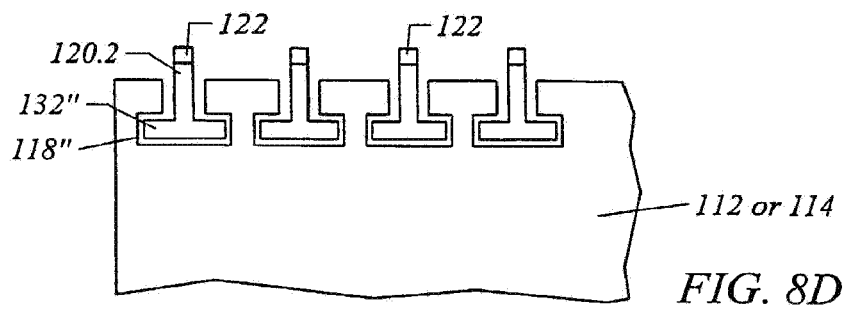

FIG. 8B illustrates one embodiment of a guideway 118 configured to accept a carriage assembly 120' or 120" as described above in FIGS. 7A and 7B. The guideway 118 includes a feature or rail 118' configured to cooperate in a sliding arrangement with the channel 132. FIG. 8C illustrates an alternative embodiment where the guideway is a raised feature 118" adapted to engage with a complementary shaped channel 132' in carriage assembly 120.1. FIG. 8D illustrates another alternative embodiment where the carriage assembly 120.2 includes a shaped feature 132" adapted to slide along within the recessed, shaped guideway 118'". In all these variations, the arrangement and shape of the complementary surfaces of the carriage assembly embodiment and the guideway embodiment are illustrative and are not intended to be limited to the examples described herein. Rather, the specific shapes used to interface the carriage assembly to the guideway may be varied accordingly as understood by one of skill in the art.

Figure 9A:
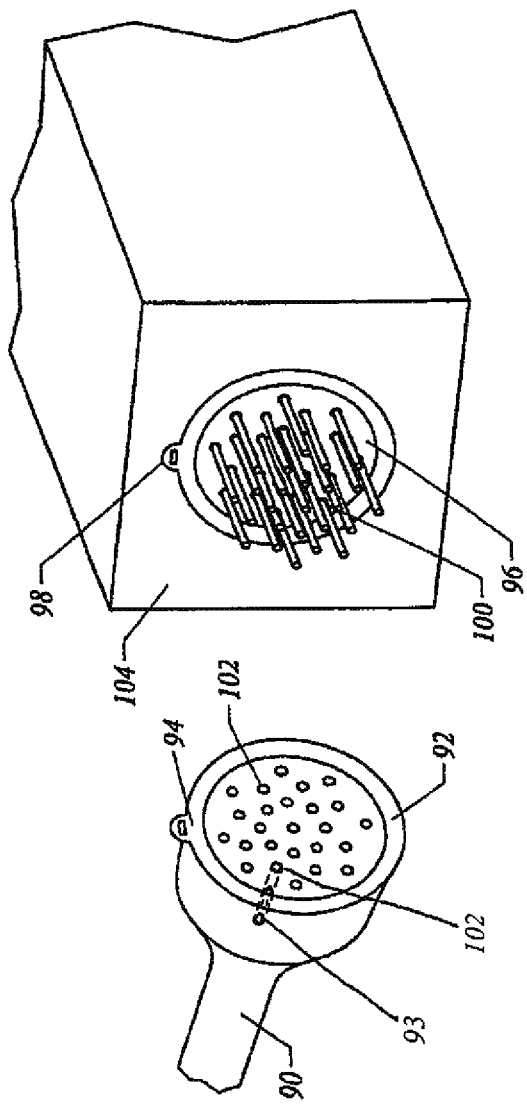
FIG. 9A shows a variation of a quick-release mechanism for attaching and detaching the tendon driven endoscope from the actuators that relies on pins to actuate the tendons.

FIGS. 9A and 9B show two variations on quick-release mechanisms for attaching and detaching an articulating instrument from a set of actuators or force generators. FIG. 9A shows one variation of this quick-release mechanism. The proximal end of the force transmission elements may be bundled in an umbilicus 90, and the individual elements may terminate in dimpled connectors 102 that are held in an organized array in a connector interface 92. For clarity only a single force transmission element 93 is shown (in phantom) within a connector 102. It is appreciated that each connector 102 could have a force transmission element 93 to mate with a corresponding pin 100. The connector interface 92 mates to a complementary receiving interface 96 on the structure that houses the actuators 104, e.g. as part of the controller box. The actuators may project "pins" 100 which can mate with the dimpled connectors and convey force from the actuators to the tendons. Thus, for example, an actuator may cause a pin 100 to apply pressure to a corresponding dimpled receiver 102. The dimpled receiver translates the pushing of the pin into a tensile or compressive force applied to the affiliated force transmission element. This could be achieved using levers to reverse the direction of the force, for example. Since every pin preferably mates to a corresponding receiver, it is desirable to maintain the register of the connectors from the endoscope and the actuators. An orientation notch 94 on the connector that fits into a receiving orientation mate 98 on the actuator could be used to align both interfaces. Alternatively, the arrangement of the pins and receptacles could be orientation specific.

This feature is not limited to pins and receptacles, since virtually any convenient mechanism for transferring force from the actuator to the force transmission elements would work. FIG. 9B shows another variation of a quick-release mechanism for attaching and detaching an articulating instrument from the actuators that relies on a nail-head configuration to actuate the force transmission elements. The force transmission elements may terminate in a flattened out protrusion resembling a nail-head 106. The array of nail-heads 106 project from the connector interface 92 at the end of the umbilicus 90, and can mate with slotted holes 108 on the interface 96 of actuator mechanism 104 (FIG. 9C). Thus the slotted holes 108 of the actuators can be individually retracted by the actuators to apply tension to individual force transmission elements. The quick-release mechanism could also be designed to allow the use of different controllable instruments, even of different configurations, from the same actuator set and/or controller unit.

Figure 10:
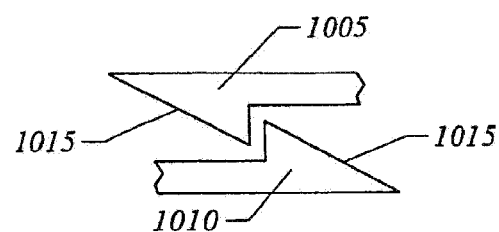
FIG. 10 illustrates an exemplary embodiment of complementary barbed connection features for force transmission elements.

FIG. 10 illustrates an embodiment of complementary barbed connection features 1005, 1010. When brought into contact, barbed connections 1005, 1010 engage and provide a force transmission pathway. These features may be used, for example, as connection points similar to nail heads 106 (FIG. 9B, 9C). These features could be configured to easily connect a force transmission element connected to an actuator to a force transmission element connected to a controllable article. For example, barb 1010 could be attached to a force transmission element connected to an actuator. Barb 1005 could be attached to a force transmission element connected to a controllable article. By causing relative movement between the barbs 1005, 1010, the complementary shaped sloped portions 1015 slide relative to each other until the barbs fall into engagement. In additional alternative embodiments, these features could also be incorporated into the design of a carriage assembly or guideway.

Figure 11:
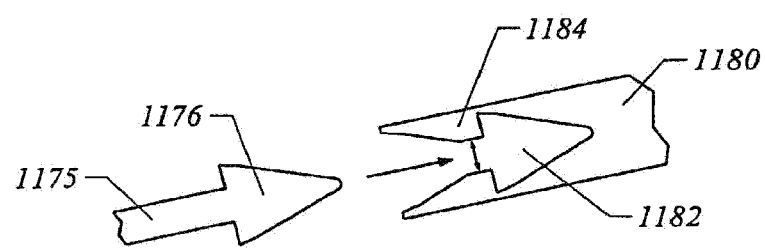
FIG. 11 illustrates an exemplary embodiment of complementary male and female connection features for force transmission elements.

FIG. 11 illustrates an embodiment of a complementary male and female engagement pair 1175, 1180. Cavity 1182 in female receiver 1180 is configured to receive the arrowhead feature 1176. As the male member 1175 is moved into contact with the female receiver 1180, the engagement tabs 1184 deflect allowing the arrowhead feature 1176 to pass into the cavity 1182. Once the arrowhead 1176 passes the engagement tabs 1184, the engagement tabs 1184 close behind the arrowhead 1176 securing it within the cavity 1182. The male/female connection features could be configured to easily connect a force transmission element connected to an actuator to a force transmission element connected to a controllable article. For example, male feature 1175 could be attached to a force transmission element connected to an actuator. Female feature 1180 could be attached to a force transmission element connected to a controllable article. Thereafter, the force transmission elements are connected by relative movement to engage the arrowhead feature 1176. In additional alternative embodiments, these features could also be incorporated into the design of a carriage assembly or guideway or as part of the embodiments of FIGS. 9A-9C.

Figure 12:
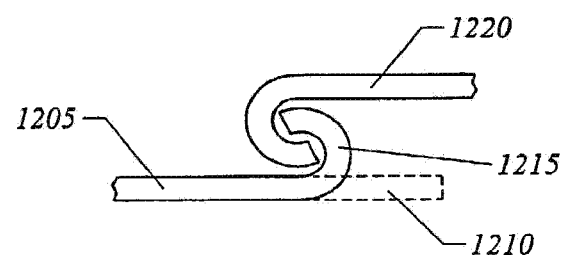
FIG. 12 illustrates an exemplary embodiment of complementary engagement element connection features for force transmission elements.

FIG. 12 illustrates an embodiment of a complementary engagement elements 1205 and 1220. SMA engagement element 1205 is formed from a shape memory alloy (SMA) or memory metal that changes configuration (martinsite to austenite and vice versa) when energy is applied to it. The unenergized state 1210 is illustrated in dashed lines. Once energized, the element curves forming hook 1215. As the SMA engagement element 1205 forms into hook 1215 it engages with the hook shaped engagement element 1220 completing the connection between the two engagement elements. The complementary engagement elements 1205 and 1220 could be configured to easily connect a force transmission element connected to an actuator to a force transmission element connected to a controllable article. For example, SMA engagement element 1205 could be attached to a force transmission element connected to an actuator. Hook 1215 could be attached to a force transmission element connected to a controllable article. Thereafter, the force transmission elements are connected by energizing the SMA element 1205 to engage the hook 1220. In additional alternative embodiments, the complementary features 1205, 1220 could also be incorporated into the design of a carriage assembly, guideway or as part of the embodiments of FIGS. 9A-9C.

Figure 13:
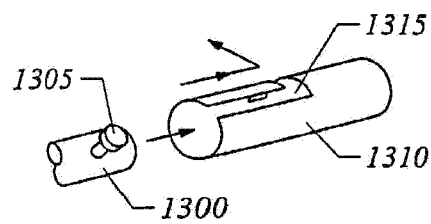
FIG. 13 illustrates an exemplary embodiment of a slotted engagement pair connection feature for force transmission elements.

FIG. 13 illustrates an embodiment of a slotted engagement pair. Male element 1300 has a feature or protrusion 1305. The slotted element 1310 includes a slot 1315 sized to receive the feature or protrusion 1305. As the male element 1300 moves in the direction indicated by the arrows, the feature or protrusion 1305 seats into and is held within the slot 1315. At this point, the male element 1300 is coupled to the slotted element 1310. The complementary engagement elements 1300 and 1310 could be configured to easily connect a force transmission element connected to an actuator to a force transmission element connected to a controllable article. For example, male element 1300 could be attached to a force transmission element connected to an actuator. Slotted element 1310 could be attached to a force transmission element connected to a controllable article. Thereafter, the force transmission elements are connected by engaging feature 1305 into slot 1315. In additional alternative embodiments, the male element 1300 and the slotted element 1310 could also be incorporated into the design of a carriage assembly, guideway or as part of the embodiments of FIGS. 9A-9C. In an alternative embodiment similar to the embodiment illustrated in FIG. 13, a window latch type connector could also be used to connect the force transmission elements. An arcuate male member could be rotated into engagement with an arcuate female member in a motion similar to the operation of a window latch.

Figure 14A:
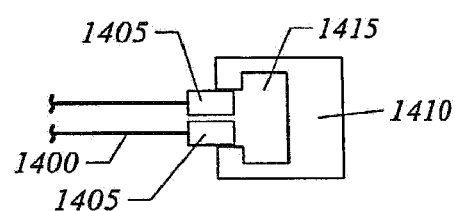
FIGS. 14A and 14B illustrate an exemplary embodiment of male and slotted engagement element connection features for force transmission elements.
Figure 14B:
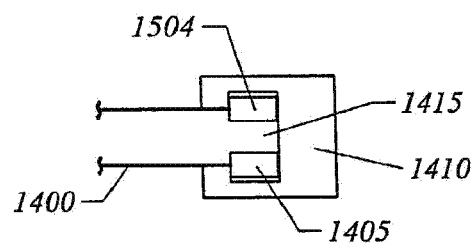

FIGS. 14A and 14B illustrate another embodiment of male 1400 and slotted 1410 engagement elements. Male engagement element 1400 includes a number of features 1405 moveable between a retracted position (FIG. 14A) and an extended or engaged position (FIG. 14B). The slotted element 1410 includes a cavity 1415 sized and shaped to retain the features 1405 when the features 1405 are in the extended position (FIG. 14B). Returning the features 1405 to a retracted position allows the male element 1400 to withdraw from the cavity 1415. The male 1400 and slotted 1410 engagement elements could be configured to easily connect a force transmission element connected to an actuator to a force transmission element connected to a controllable article. For example, male element 1400 could be attached to a force transmission element connected to an actuator. Slotted element 1410 could be attached to a force transmission element connected to a controllable article. Thereafter, the force transmission elements are connected by engaging features 1405 into cavity 1415. In additional alternative embodiments, the male element 1400 and the slotted element 1410 could also be incorporated into the design of a carriage assembly, guideway or as part of the embodiments of FIGS. 9A-9C.

Figure 15:
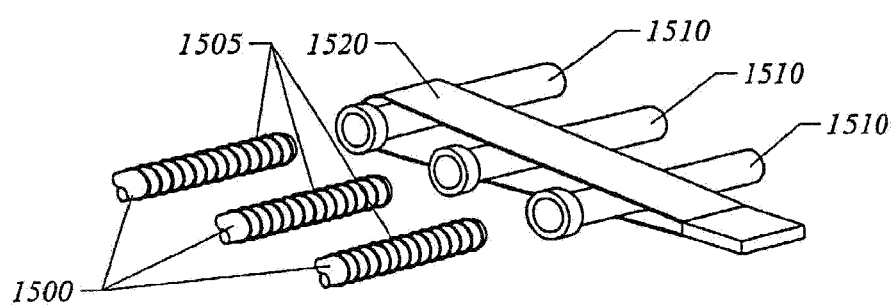
FIG. 15 illustrates an exemplary embodiment of a complementary engagement pair including threaded male and female connection members for force transmission elements.

FIG. 15 illustrates a complementary engagement pair including threaded male members 1500 and correspondingly threaded female receivers 1510. Threaded male members 1500 include threads 1505. Correspondingly threaded female receivers 1510 have internal threaded surfaces (not shown) to engage the threads 1505 on male members 1500. Also illustrated is an embodiment of a driver 1520 that is wrapped about or otherwise coupled to the female receivers 1510. In operation, the driver 1520 rotates the female receivers 1510 to engage threads 1505 and secure together the male member 1500 into the female receiver 1510. While illustrated as the female receiver 1510 rotating about a stationary male member 1500, the driver 1520 may also be configured to rotate the male members 1500 to drive threads 1505 into stationary female receivers 1510. It is to be appreciated that three pairs 1500, 1510 are illustrated for discussion purposes only. The principal of engagement represented by the pairs 1500, 1510 may be applied to any number of pairs. The male threaded 1500 and female threaded 1510 engagement elements could be configured to easily connect a force transmission element connected to an actuator to a force transmission element connected to a controllable article. For example, male threaded element 1500 could be attached to a force transmission element connected to an actuator. Female threaded element 1510 could be attached to a force transmission element connected to a controllable article. Thereafter, the force transmission elements are connected by engaging threads 1505 into threaded interior features of female threaded element 1510 through, in one embodiment, rotation via driver 1520 of the female threaded elements 1520. In additional alternative embodiments, the threaded male element 1500 and the threaded female element 1510 could also be incorporated into the design of a carriage assembly, guideway or as part of the embodiments of FIGS. 9A-9C.

Figure 16:
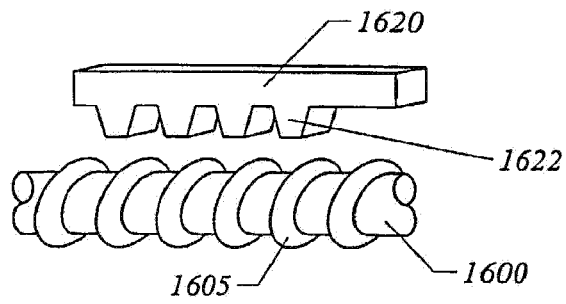
FIG. 16 illustrates an exemplary embodiment of an engagement and force transmission coupling for force transmission elements.

FIG. 16 illustrates an alternative engagement and force transmission coupling that utilizes a carriage assembly 1620 and a threaded driver 1600 in a worm gear configuration. The carriage assembly 1620 is similar in design and function as the above described carriage assemblies 120. Carriage assembly 1620 differs in at least that the engagement features 1622 are shaped and sized to engage and transfer force from the threads 1605 as the drive member 1600 rotates. Guideways 118 may be modified to accommodate and ensure engagement of the drive member 1600 and carriage assembly 1620 when the first and second connector portions 112, 114 engage. In one embodiment, an actuator or force generator causes the driver 1600 to rotate. The threads 1605 are engaged with the features 1622 such that as the driver 1600 rotates the carriage assembly 1620 translates relative to the driver 1600.

Figure 17:
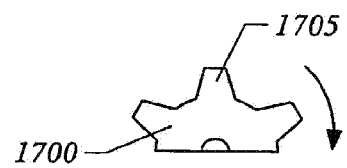
FIG. 17 illustrates an exemplary embodiment of a gear drive or half spur drive coupling for force transmission elements.

FIG. 17 illustrates another alternative gear drive or half spur drive configuration. This alternative engagement and force transmission coupling utilizes a carriage assembly 1720 and a spur driver 1700. The carriage assembly 1720 is similar in design and function as the above described carriage assemblies 120. Carriage assembly 1720 differs in at least that the engagement features 1722 are shaped and sized to engage and transfer force from the spur engagement elements 1705 as the spur drive 1700 rotates. In one aspect of the illustrated embodiment, the spur drive 1700 is coupled to an actuator and the carriage assembly 1720 is coupled to a controllable article. The spur drive 1700 may be used simply to engage with the carriage assembly 1720 by rotating in the direction indicated. Thereafter, the spur driver 1700, coupled to the carriage assembly 1720, translates along a guideway as described above and thereby articulates the controllable article. In an alternative embodiment, the spur driver 1700 is larger, perhaps, even a complete gear, that instead of coupling to and translating with the carriage assembly 1720, the gear drive 1700 would be engaged with and rotate relative to the carriage assembly 1720. Rotation of the gear drive 1700 in this alternative embodiment would result in translation of the carriage assembly 1720 and articulation of the controllable article. In each of these embodiments, guideways 118 may be modified to accommodate and ensure engagement of the gear drive 1700 and carriage assembly 1720 when the first and second connector portions 112, 114 engage. In one embodiment, an actuator or force generator causes the gear driver 1700 to rotate. The engagement elements 1705 are engaged with the features 1722 such that as the gear driver 1700 rotates the carriage assembly 1620 translates relative to the gear driver 1700.

Figure 18A:
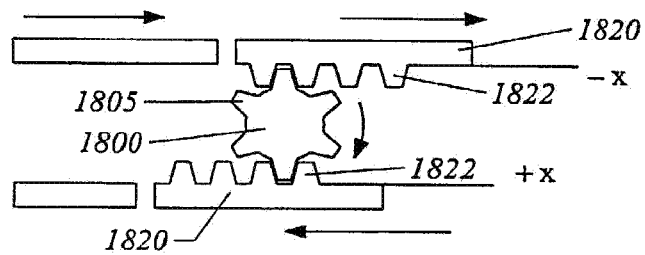
FIGS. 18A and 18B illustrate an exemplary embodiment of a gear drive engagement and force transmission coupling.
Figure 18B:
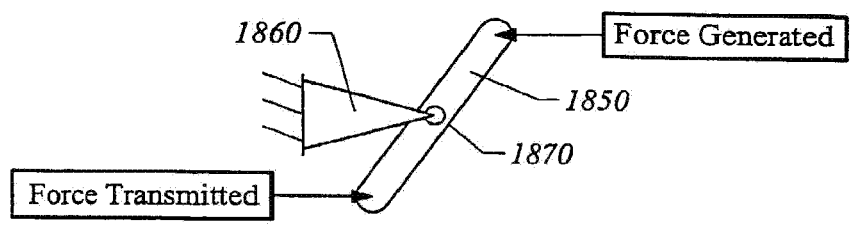

FIG. 18A illustrates another alternative gear drive configuration. This alternative engagement and force transmission coupling utilizes carriage assemblies 1820 and a gear driver 1800. The transmission of force follows similar to the manner in which pushing on one end of a bar 1850 hinged to a fulcrum 1860 by a pivot point 1870 results in movement of the other end of the bar (FIG. 18B). Returning to FIG. 18A, the carriage assemblies 1820 is similar in design and function as the above described carriage assemblies 120. A carriage assembly 1820 differs in at least that the engagement features 1822 are shaped and sized to engage with the gear teeth 1805 as the gear drive 1800 rotates. In one aspect of the illustrated embodiment, one carriage assembly 1820 is coupled to an actuator and the other carriage assembly 1820 is coupled to a controllable article. An actuator or force generator moves its carriage assembly that in turn engages teeth 1805 to rotate gear 1800. Rotation of gear 1800 engages teeth 1805 with the other carriage assembly 1820 resulting in translation of that carriage assembly and movement of the controllable article. In an alternative embodiment, the gear driver 1800 would instead be used as a driver to cause translation of both carriage assemblies 1820. Rotation of the gear drive 1800 in this alternative embodiment would result in translation of both carriage assemblies 1820 and articulation of the controllable article. In each of these embodiments, the first and second connector portions 112, 114 and the guideways 118 may be modified to accommodate and ensure engagement of the gear drive 1800 and carriage assemblies 1820 when the first and second connector portions 112, 114 engage.

FIG. 19 illustrates an alternative method of engaging the actuator to a force transmission element. A force transmission element 1915 has a catch 1910. The actuator 1900 is connected to and maneuverable by a linkage 1905. In operation, the linkage 1905 moves the actuator 1900 as indicated into engagement with the catch 1910. Once the actuator 1900 is coupled to the catch 1910, forces generated by the actuator 1900 result in translation of the force transmission element 1915. In additional alternative embodiments, the linkage 1905, actuator 1900 and catch 1910 elements could also be incorporated into the design of a carriage assembly, guideway or as part of the embodiments of FIGS. 9A-9C.

FIGS. 20A and 20B illustrate one embodiment of an engagement system to engage a connector embodiment of the present invention. An L-shaped frame 2010 includes a guide 2015 for an upper plate 2020. An actuator 2000 is coupled to the upper plate 2020 to move the upper plate up and down the guide 2015. In this embodiment, the motion of the upper plate 2020 is the motion that engages the first and second connector portions 112, 114. The upper plate 2020 has a lower surface 2025 including a first connector portion 118. The L-shaped frame upper surface 2030 also includes a first connector portion 118. A double sided connector portion 114 is placed between the plates (FIG. 20B). With the double sided second connector portion 114 disposed between the plates (FIG. 20B), the actuator 2000 moves the upper plate 2020 to engage the carriage assemblies of each of the connector assemblies in the connection portions an complete the connection from the force generator to the controllable article. While illustrated as engaging one double sided second connector portion 114, it is to be appreciated that this embodiment could be modified to connect one or more single sided second connectors 114 or two or more double sided second connector portions 114 by including single or double sided first connector portions 112 as needed.

FIG. 21 illustrates a pair of force transmission elements 2110. Force transmission elements 2110 are similar in many ways to the earlier described force transmission elements. Force transmission elements 2110 differ from the earlier described elements in that the ends 2115 are shaped and configured to attach the elements 2110 together using vacuum or suction forces. In additional alternative embodiments, the vacuum or suction end 2115 could also be incorporated into the design of a carriage assembly, guideway or as part of the embodiments of FIGS. 9A-9C.

Figure 22A:
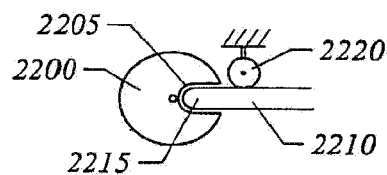
FIGS. 22A and 22B illustrates an exemplary embodiment of a connection and force transmission arrangement.
Figure 22B:
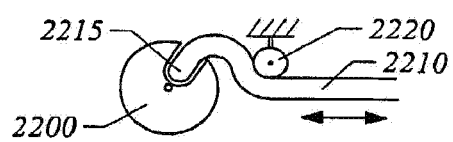

FIGS. 22A and 22B illustrate an alternative connection and force transmission arrangement. An actuator 2200 has a recess 2205 adapted to receive and secure an end 2215 of a force transmission element 2210. Another part of the force transmission element 2210 is connected to a controllable article. When the end 2215 is seated in recess 2205, the force transmission element is also secured against a fixed roller 2220. Movement of the force translation element is accomplished by rotation of the actuator 2200 resulting in deflection of the force transmission element 2210 about the actuator 2200 and against the roller 2220. In one embodiment, the guideways of a connector portion could each contain an actuator 2200. The other connector portion could contain force transmission elements 2210 having ends 2215. In this embodiment, coupling together the connector portions would urge the end 2215 into engagement with the recess 2205 thereby providing a force transmission pathway. In additional alternative embodiments, the actuator 2200, recess 2205 and end 2215 could also be incorporated into additional alternative designs of a carriage assembly, guideway or as part of the embodiments of FIGS. 9A-9C.

Figure 23:
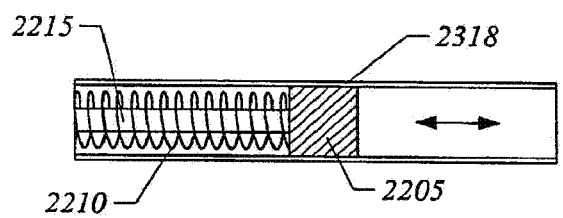
FIG. 23 illustrates an exemplary embodiment of a connector assembly utilizing a pressure source.

FIG. 23 illustrates an embodiment of a connector assembly modified to utilize a pressure source 2300 as a force generator. A pressure source capable of generating positive and negative pressure is connected to a modified pressure tight guideway 2318 containing a piston 2205. Piston 2205 is in a sealed and slideable relation to the interior of the guideway 2318. The piston 2205 is also connected to a bias element 2210 and force transmission element 2215. The force transmission element is also connected to a controllable article. In operation, pressure changes generated by the pressure source 2200 result in the translation of the piston

2205. Translation of the piston 2205 results in the translation of the force transmission element 2215 and the movement of the controllable article.

Figure 24:
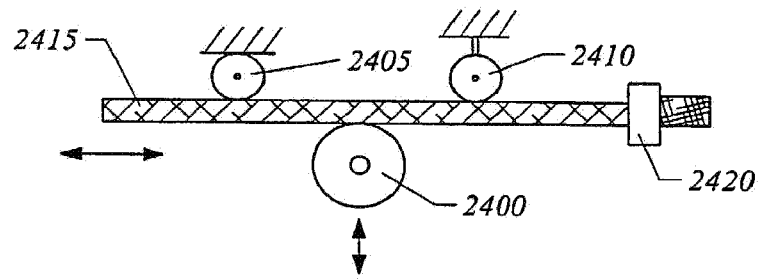
FIG. 24 illustrates an exemplary embodiment of a roller actuator to couple and drive a force transmission element.

FIG. 24 illustrates another embodiment of a roller actuator operation set used to couple to and drive a force transmission element. A roller actuator set includes a roller actuator 2400 and a pair of fixed rollers 2405, 2410. The roller actuator 2400 may move in the indicated directions. Movement towards the force transmission element 2415 will engage the element 2415. Since the element is secured against block 2420, further moving actuator 2400 deflects the element between the rollers 2405, 2410 resulting in movement of element 2415. In an alternative embodiment, another operating set of a roller actuator 2400 and roller pair 2405, 2410 may be utilized in opposition to the described actuator and roller. In this embodiment, one actuator and roller pair moves the force transmission element in a first direction while the other actuator is idle. To move the element in the opposite direction, the other actuator is activated to deflect the element while the one actuator idles. In additional alternative embodiments, the actuator 2400, and rollers 2405, 2410 (in one or more operating sets) could also be incorporated into additional alternative designs of a carriage assembly, guideway or as part of the embodiments of FIGS. 9A-9C.

FIGS. 31A, 31B and 31C illustrate a complementary engagement pair including saw tooth male member 3100 and correspondingly shaped saw tooth female receiver 3120. Saw tooth male member 3100 includes individual saw teeth 3105. Correspondingly shaped female saw tooth receivers 3122 are shaped to engage the saw teeth 3105 on male member 3100. FIG. 31A illustrates the members 3100, 3120 in a disengaged configuration. Longitudinal movement between the members 3100, 3120 places the members in an engaged position (FIG. 31B). In this configuration, force, position and lateral translation may all be conveyed between the members 3100, 3120. Disengagement of the members is illustrated in FIG. 31C. Rotation of one member relative to the other is used to disengage the members. In the illustrated embodiment, the female member 3120 is rotated in the direction indicated to move the female teeth 3122 out of engagement with the male saw teeth 3105. In other alternative embodiments, different saw tooth shapes may be used or other shapes suited to longitudinal engagement and rotational disengagement may be used. In addition, the male member 3100 may be rotated to disengage engaged members 3100, 3120.

Any of the above connection embodiments may be modified to include sensors to provide added functionality to embodiments of the connector of the present invention. Sensors may be located in either or both of the connector portions 112, 114 or in any of the connection and release mechanisms described herein. Any of a wide variety of commonly available sensors may be used to accomplish the functionalities described below such as, for example, reed switches, electro-optical switches, resistive switches, contact switches, optical indicators, strain gauges, stress gauges, measurement indicators and the like. Examples of added functionality, include without limitation, detection of cable or carriage assembly translation, position, or engagement With regard to engagement, sensors may be used to indicate proper or improper engagement between carriage assemblies or connectors or whether components have become or are about to become disengaged. Sensors may be used to measure component performance or failure. For example, a sensor detects when a cable becomes slack when it should be under tension as an indication of cable failure or, if a carriage assembly suddenly locks into a position, a sensor may indicate an obstruction of the controllable article and/or obstruction or abnormal occurrence elsewhere in the force transmission pathway. Additionally, the output or signal from a sensor may be integrated into the control system. For example, sensors within the connector could be used to measure carriage assembly movement as the indication for position of the controllable article. The sensor could be coupled to or in communication with a portion of the connector assembly and have an output that indicates the position of the instrument. Furthermore, the control system could be adapted to use the output of the sensor, in place of or in addition to encoders on the instrument to control and/or monitor the position, shape, movement etc. of the instrument.

In a specific example where the controllable article is a steerable endoscope, the tip of the endoscope and different segments or positions of the endoscope could be controlled using the position of the carriage assembly/assemblies and cables used to control those segments. In another example, a sensor may be used as limit switch for the length of travel of a carriage assembly. In this example, the carriage assembly length of travel corresponds to a physical or operational limitation of the system or of the controllable article. As such when the carriage assembly reaches the limit switch the control system may respond appropriately by, for example, shutting off power, sounding an alarm or otherwise providing an indication that the limit switch sensor had been activated. In addition, sensors may be used to identify a particular controllable article being provided to the connector. The identifying information could be used to recall stored maintenance or performance information about the particular controllable article. If for example, a particular component was beginning to wear or if a particular cable required additional force for proper movement such unique variability for the article could be provided to and accounted for by the control signals generated by the control system. Likewise, the control system may have recording capabilities to record the amount of time the device was used and performance criteria met or not met by the article. In another example, a connector portion attached to a controllable article may include a sensor, other readable feature, mark or other identifying characteristic or a user may enter a serial number or the connector may have a bar code identifier read by a bar code reader associated with the system. The system could automatically read the identifying feature of the connector and adjust control signals according to the stored maintenance, performance and/or service information related to that article.

Embodiments of the connector of the present invention allow for determination of position and provide control of the various segments or modules of a controllable article using the position and/or movement of the cables or carriage assemblies or other components within the connector. For example, the position, shape, and/or movement of the tip of a steerable endoscope or portion thereof could be controlled using the position of the cables, carriage assemblies or other components used to control the tip. The amount of within connector movement of the more or more cables, carriage assemblies or components is correlated to an amount, degree or type of tip movement. A such, by monitoring and controlling within connector movements, the tip and other sections or modules of a controllable article may be controlled. Additionally, linear motion of the cable within the connector may be used to indicate segment position including the position and movement of the instrument tip. Sensors to detect movement may be placed in one or both connector portions 112, 114 (or in other connector assemblies such as FIG. 20B or as described herein)

In addition, sensors incorporated into the connector may be used to measure or indicate the operational condition of the cables, cable wear or changes in friction loads in the instrument. For example, sensors in the connector may be used to detect, for example, increases in cable wear or friction within the instrument, in specific cables and sections of the instrument. Information regarding the operating condition of the cables and instrument may be used in a number of ways to improve overall system performance. For example, measurements indicating increasing friction losses over a period of time may be used as an indication that maintenance or service of the instrument is advisable. Alternatively, measurements indicating an immediate friction increase may be an indication of mechanical binding in the force transmission pathway, instrument failure or that the instrument has encountered an obstruction. The signal indications could be used by the system in a number of ways, such as for example, a warning indication, a safety shut-offs, or a "service needed" indicator.

Figure 25:
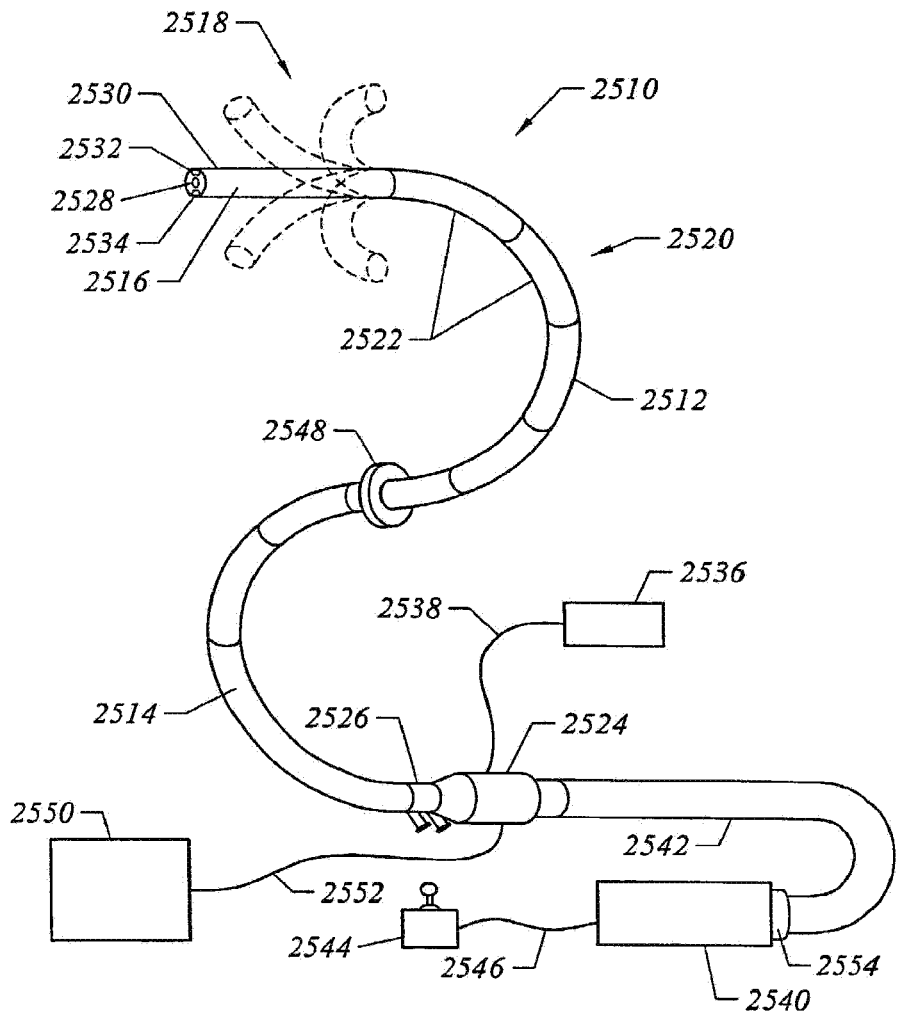
FIG. 25 illustrates an embodiment where the controllable article is a segmented endoscope.

FIG. 25 shows an embodiment where the controllable article is a tendon driven endoscope 2510. The endoscope 2510 has an elongate body 2512 with a manually or selectively steerable distal portion 2516, an automatically controlled portion 2520, and a flexible and passively manipulated proximal portion 2514, which may be optionally omitted from the device. The steerable distal portion 2516 can be articulated by hand (i.e., using mechanical force of a conventional endoscope manual controls adapted to articulate segments) or with mechanical assistance from actuators. In addition, some embodiments allow a user to input steering commands (i.e., via a joystick 2544 or other input device) into a controller that translates the steering commands into endoscope segment movement.

The automatically controlled portion 2520 is segmented, and each segment is capable of bending through a full range of steerable motion. The distal portion 2516 is also a controllable segment. A more detailed description on the construction and operation of the segmented endoscope may be found in U.S. patent application Ser. No. 10/229,577 filed Aug. 27, 2002, which is incorporated herein by reference in its entirety.

The selectively steerable distal portion 2516 can be selectively steered or bent up to, e.g., a full 180° bend in any direction 2518, as shown. A fiber optic imaging bundle 2534 and one or more illumination fibers 2532 may extend through the body 2512 from the proximal portion 2514 to the distal portion 2516. Alternatively, the endoscope 2510 may be configured as a video endoscope with a miniaturized video camera, such as a CCD or CMOS camera, positioned at the distal portion 2516 of the endoscope body 2512. The images from the video camera can be transmitted to a video monitor by a transmission cable or by wireless transmission where images may be viewed in real-time and/or recorded by a recording device onto analog recording medium, e.g., magnetic tape, or digital recording medium, e.g., compact disc, digital tape, etc. LEDs or other light sources could also be used for illumination at the distal tip of the endoscope.

The body 2512 of the endoscope 2510 may also include one or more access lumens 2528 that may optionally be used for illumination, fibers for providing a light source, insufflation or irrigation, air and water channels, and vacuum channels. Generally, the body 2512 of the endoscope 2510 is highly flexible so that it is able to bend around small diameter curves without buckling or kinking while maintaining the various channels intact. When configured for use as a colonoscope, the body 2512 of the endoscope 2510 may range typically from 135 to 185 cm in length and about 13-19 mm in diameter. The endoscope 2510 can be made in a variety of other sizes and configurations for other medical and industrial applications.

The controllable portion 2520 is composed of at least one segment 2522, and preferably several segments 2522, which are controllable via a computer and/or electronic controller 2540 located at a distance from the endoscope 2510. Each, or at least a majority, of the segments 2522 may have forces transmission elements or tendons mechanically connected to force generators or actuators to allow for the controlled motion of the segments 2522 in space. The actuators driving the tendons may include a variety of different types of mechanisms capable of applying a force to a tendon, e.g., electromechanical motors, pneumatic and hydraulic cylinders, pneumatic and hydraulic motors, solenoids, shape memory alloy wires, electronic rotary actuators or other devices or methods as known in the art. If shape memory alloy wires are used, they are preferably configured into several wire bundles attached at a proximal end of each of the tendons within the controller. Segment articulation may be accomplished by applying energy, e.g., electrical current, heat, etc., to each of the bundles to actuate a linear motion in the wire bundles which in turn actuate the tendon movement. The linear translation of the actuators within the controller may be configured to move over a relatively short distance, e.g., within a few inches or less such as ±1 inch, to accomplish effective articulation depending upon the desired degree of segment movement and articulation.

It is preferable that the length of the insertable portion of the endoscope comprises controllable segments 2522, although a passive proximal portion 2514 can also be optionally used. This proximal portion 2514 is preferably a flexible tubing member that may conform to an infinite variety of shapes, and may be made from a variety of materials such as thermoset and thermoplastic polymers which are used for fabricating the tubing of conventional endoscopes.

Each segment 2522 preferably defines at least one lumen running throughout to provide an access channel through which wires, optical fibers, air and/or water channels, various endoscopic tools, or any variety of devices and wires may be routed. A polymeric covering, or sheath, 2530 may also extend over the body of the endoscope 2512 including the controllable portion 2520 and steerable distal portion 2516. This sheath 2530 can preferably provide a smooth transition between the controllable segments 2522, the steerable distal portion 2516, and the flexible tubing of proximal portion 2514.

A handle 2524 may be attached to the proximal end of the endoscope. The handle 2524 may include an ocular connected to the fiber optic imaging bundle 2534 for direct viewing. The handle 2524 may otherwise have a cable 2552 for connection to a video monitor; camera, e.g., a CCD or CMOS camera, or a recording device 2550. The handle 2524 may be connected to an illumination source 2536 by an illumination cable 2538 that is connected to or continuous with the illumination fibers 2534. Alternatively, some or all of these connections could be made at the controller 2540. Luer lock fittings 2526 may be located on the handle 2524 and connected to the various instrument channels.

The handle 2524 may be connected to a motion controller 2540 by way of a controller cable 2542. A steering controller 2544 may be connected to the motion controller 2540 by way of a second cable 2546 or it may optionally be connected directly to the handle 2524. Alternatively, the handle may have the steering control mechanism integrated directly into the handle, e.g., in the form of a joystick, conventional disk controllers such as dials, pulleys or wheels, etc. The steering controller 2544 allows the user to selectively steer or bend the selectively steerable distal portion 2516 of the body 2512 in the desired direction 2518. The steering controller 2544 may be a joystick controller as shown, or other steering control mechanism, e.g., dual dials or rotary knobs as in conventional endoscopes, track balls, touchpads, mouse, or sensory gloves. The motion controller 2540 controls the movement of the segmented automatically controlled proximal portion 2520 of the body 2512. This controller 2540 may be implemented using a motion control program running on a microcomputer or using an application-specific motion controller. Alternatively, the controller 2540 may be implemented using, e.g., a neural network controller.

The actuators applying force, to the tendons may be included in the motion controller unit 2540, as shown, or may be located separately and connected by a control cable. The tendons controlling the steerable distal portion 2516 and the controllable segments 2522 extend down the length of the endoscope body 2512 and connect to the actuators. FIG. 25 shows a variation in which the tendons may pass through the handle 2524 and connect directly to the motion controller 2540 via a quick-release connector 2554. In this embodiment, quick release connector 2254 could be any of the above described connector or engagement assemblies. In this variation, the tendons may be part of the control cable 2542, although they could independently connect to the actuators, so long as the actuators are in communication with the controller 2540.

An axial, motion transducer (also called a depth referencing device or datum) 2548 may be provided for measuring the axial motion, i.e., the depth change, of the endoscope body 2512 as it is advanced and withdrawn. The depth referencing device 2548 can be made in many possible configurations. For example, the axial motion transducer 2548 in FIG. 25 is configured as a ring 2548 that may surround the body 2512 of the endoscope 2510. The axial motion transducer 2548 is preferably attached to a fixed point of reference, such as the surgical table or the insertion point for the endoscope 2510 on the patient's body. Depth referencing device 2548, and different examples thereof, as well as segment articulation and cable operation are described in further detail in U.S. patent application Ser. No. 10/229,577 filed Aug. 27, 2002, which is incorporated herein by reference in its entirety.

Figure 26:
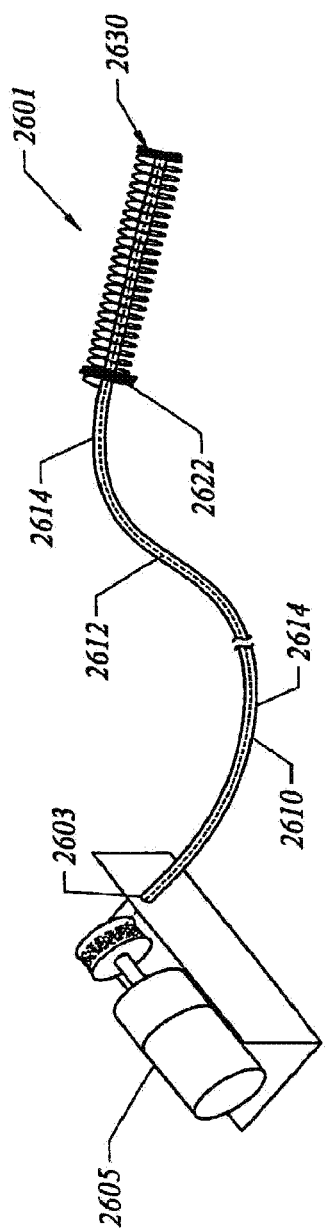
FIG. 26 shows a partial schematic representation of a single tendon bending a segment.

FIG. 26 shows a partial schematic representation of a single tendon bending a segment. For clarity, the other parts of a complete endoscope, including other tendons and segments, have been omitted from FIG. 26. Tension applied to a tendon cable is transferred across the entire segment, resulting in bending. The Bowden cable 2610 has a sleeve 2614 attached to the base 2622 of the segment 2601 and also fixed at the proximal actuator end 2603. The tendon cable 2612 is connected to the actuator 2605 and the distal segment end 2630. By applying tension to the tendon 2612, only the intended segment 2601 is bent, and more proximal segments are unaffected. The tendon 2612 is placed in tension by the actuator 2605, which is shown, in this variation, as a motor pulling on the tendon cable 2612.

Figure 27A:
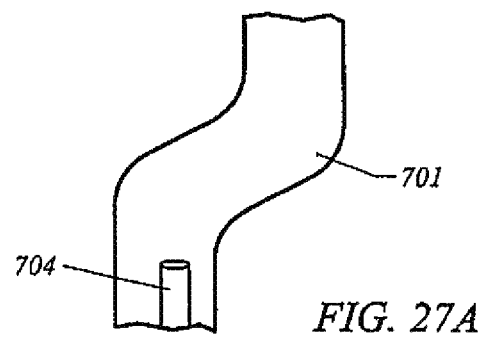
FIGS. 27A, 27B and 27C illustrate an endoscope traversing a pathway.
Figure 27B:
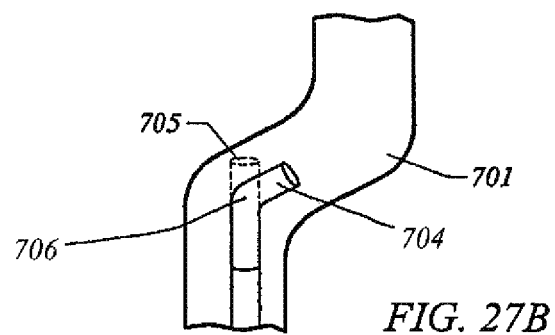
Figure 27C:
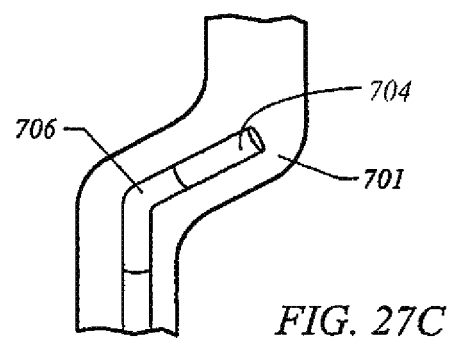

FIGS. 27A to 27C illustrate a variation of the tendon driven endoscope navigating a tortuous path. The path 701 is shown in FIG. 27A. This pathway may represent a portion of colon, for example. In FIG. 27A, the distal tip of the device 704 approaches the designated bend. FIG. 27B shows the distal tip being steered 705 (i.e., from the phantom position to the solid position) to assume the appropriate curve or bend 706. This steering could be performed manually by the user, e.g. a doctor, or automatically using an automatic detection method that could determine the proximity of the walls of the pathway or using images of the pathway generated by the instrument alone or in combination with images generated by an imaging modality outside of the instrument. As described, the bending of the steerable tip is performed by placing tension on the tendon, or combination of tendons that results in the appropriate bending.

The device is then advanced again in FIG. 27C; as it is advanced, the selected curve is propagated down the proximal length of the endoscope, so that the bend 706 of the endoscope remains in relatively the same position with respect to the pathway 701. This prevents excessive contact with the walls, and allows the endoscope to move more easily along the tortuous pathway 701. The endoscope is in continuous communication with the motion controller, and the motion controller can monitor the location of the endoscope within the pathway, e.g., depth of insertion, as well as the selected bends or curves that define the pathway of the endoscope. Depth can be determined by, e.g., the axial motion transducer 2548 previously described, or by more direct measurement techniques. Likewise, the shape of each segment could be determined by the tension applied to the tendons, or by direct measurement, such as direct measurement of displacement of the tendon cables. The motion controller can propagate the selected shape of a segment at a specified location, or depth, within the body, e.g., by setting the lengths of the sides of more proximal segments equal to the corresponding lengths of the sides of more distal segments as the device is moved distally. The controller can also use this information to automatically steer the body of the endoscope, or for other purposes, e.g. creating a virtual map of the endoscope pathway for analytic use.

In addition to measuring tendon displacement, the motion controller alone, a connector of the present invention alone or the controller and the connector operating together can also adjust for tendon stretch or compression. For example, the motion controller can control the "slack" in the tendons, particularly in tendons that are not actively under tension or compression. Allowing slack in inactive tendons reduces the amount of force that is required to articulate more proximal segments. In variations described above, the umbilicus at the distal end of the endoscope may contain space to allow slack in individual tendons.

The bending and advancing process can be done in a stepwise or continuous manner. If stepwise, e.g., as the tendon is advanced by a segment length, the next proximal segment 706 is bent to the same shape as the previous segment or distal steerable portion. A more continuous process could also result by bending the segment incrementally as the tendon is advanced. This could be accomplished by the computer control; for example when the segments are smaller than the navigated curve.

Figure 28:
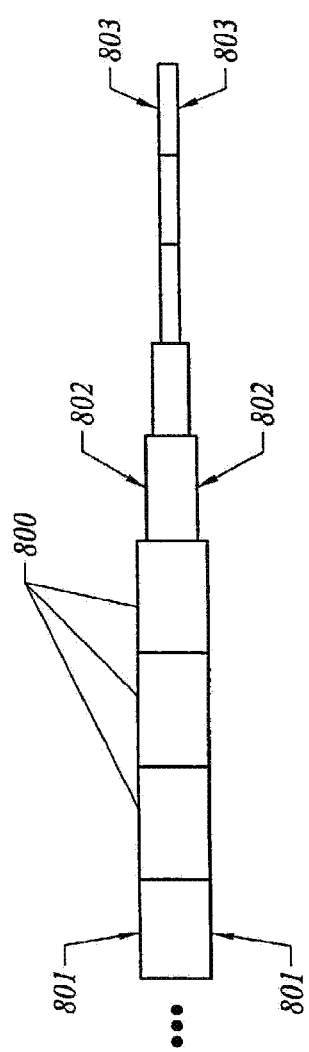
FIGS. 28 and 29 illustrate alternative endoscope embodiments.
Figure 29:
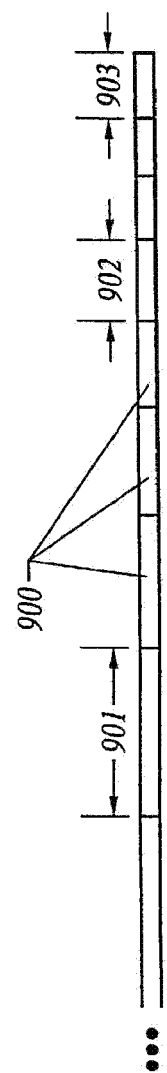

Controllable segments, including the steerable distal portion, can be selected to have different dimensions, e.g., different diameters or lengths, even within the same endoscope. Segments of different dimensions may be desirable because of considerations of space, flexibility and method of bending. For example, the more segments in an endoscope, the further it can be steered within a body cavity; however, more segments require more tendons to control the segments. FIGS. 28 and 29 illustrate two variations on tendon driven endoscopes.

FIG. 28 shows a tendon driven endoscope variation that has segments 800 of differing diameters. More distal segments may have a smaller diameter 803 than more proximal segments, e.g., 802, 801. The diameter of a typical endoscope could decrease from, e.g., 20 mm, down to, e.g., 12.5 mm. The endoscope shown in FIG. 28 appears telescoped, as the diameter decreases distally in a stepwise manner. This design would be responsive, e.g., to internal body structures that become increasingly narrow. This design would also help accommodate bypassing tendons from more distal segments as they proceed towards the proximal actuators because of the larger diameter of the more proximal segments. FIG. 28 shows four differently sized segments; however, virtually any number of differently sized segments could be used. Moreover, although the segments appear stepped in this variation, the outer surface may be gently tapered to present a smooth outer surface decreasing in diameter towards the distal end.

FIG. 29 shows another variation of the tendon driven endoscope that has segments of different lengths. Using segments of different lengths may require fewer overall segments 900 to construct an equivalent length of articulatable endo scope. As shown in FIG. 29, more proximal segments 901 are increasingly longer than more distal, e.g., 902, 903, segments. For example, segment length could be decreased from 20 cm at a proximal segment down to 6 cm at a distal most segment. The lengths may be decreased incrementally segment to segment by a constant factor; alternatively, lengths may be decreased geometrically, exponentially, or arbitrarily depending upon the desired articulation. In practice this results in an "averaging" of curves by more distal segments as bends and turns are propagated proximally. In order to accomplish this, the motion controller may be configured to accommodate the differently sized segments accordingly. Alternatively, endoscopes could be comprised of a combination of segments of different length and thickness, depending upon the application.

The tendons that articulate the segments are in mechanical communication with the actuators. However, it may be desirable to have the insertable distal portion of the endoscope be removable from the actuators and controller, e.g., for cleaning or disinfecting. A quick-release mechanism, such as a connector embodiment described in this application, between the proximal end of the endoscope and the actuators is an efficient way to achieve an endoscope that is easily removable, replaceable or interchangeable. For example, the proximal ends of the tendons can be organized to allow predictable attachment to corresponding actuators, such as for example, through the utilization of embodiments of connector portions 112, 114 or the connectors described with regard to FIGS. 9A and 9B. In addition, the connector provides ways for the tendons to be organized into a bundle, array, or rack. This organization could also provide other advantages to the endoscope, such as allowing active or passive control of the tendon slack. Furthermore, the proximal ends of each tendon can be modified to allow attachment and manipulation, e.g., the ends of the tendons may be held in a specially configured sheath or casing such as through the use of any of the above described connector and engagement embodiments.

Figure 30A:
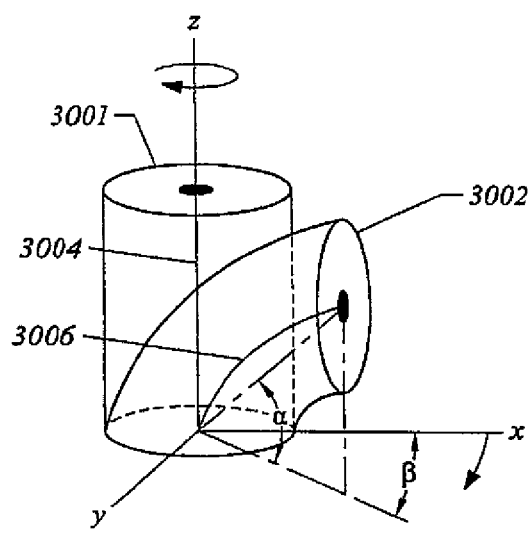
FIGS. 30A, 30B, 30C, 30D, 30E, and 30F show the use of three tendons to actuate a controllable segment used in the endoscope of the present invention.

FIG. 30A shows an example of the resulting segment articulation which may be possible through the use of two or three tendons to articulate the controllable segments, including the steerable distal section. FIG. 30A shows one example of a possible range of motion of controllable segment of the present disclosure actuated, in this example, by three tendons. A segment in the relaxed, upright position 3001 can be bent in virtually any direction relative to the x-y plane. FIG. 30A, as an illustrative example, shows a segment 3002 that has been bent down and at an angle relative to its original position 3001. The angles $\alpha$ and $\beta$ describe the bend assumed by the segment. Angle $\beta$ gives the angle in the x-y plane, while $\alpha$ is the angle describing the motion in the x-z plane. In one variation, the controllable segments of the endoscope can bend through all 360 degrees in the $\beta$ angle and up to 90 degrees in the $\alpha$ angle. An angle $\alpha$ greater than 90 degrees would result in looping of the endoscope. In FIG. 30A, the segment 3002 is shown bent approximately 45 degrees along angle $\alpha$. The freedom of movement of a segment is, in part, determined by the articulation method, the size of the segment, the materials from which it is constructed, and the manner in which it is constructed; among others. Some of these factors are discussed herein.

The steerable distal portion, as well as the endoscope and the controllable segments are bendable but preferably not compressible or expansible. Thus, in FIG. 30A, the centerline 3004 of the relaxed segment 3001 is approximately the same length as the centerline 3006 of the segment after bending 3002.

Figure 30B:
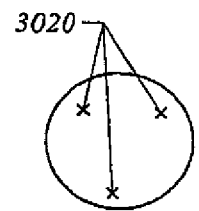
Figure 30C:
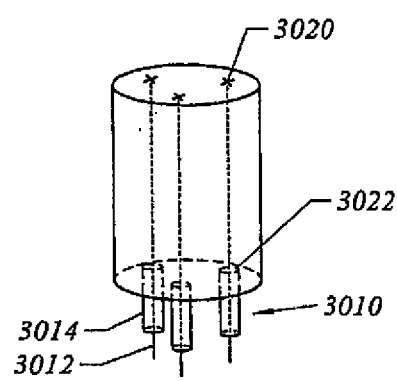

FIGS. 30B to 30F show the use of three tendons to actuate a controllable segment used in an endoscope of the present disclosure. The tendons shown in this example are all Bowden type cables 3010 that have an internal cable 3012 coaxially surrounded by a housing or sleeve 3014 in which the cable is free to move. Bowden cables can be used to apply either tensile or compressive forces, i.e., they may be pushed or pulled, to articulate the endoscope and can be actuated remotely to deliver forces as desired at locations along the endoscope. Force from a tendon is exerted across or through the segment by attaching the tendon cable at the distal end of the segment 3020 and the tendon housing 3014 at the proximal end of the segment 3022, as depicted in FIG. 30C. FIG. 30B shows a view of the top of the segment with three attachment sites for the tendon cables indicated 3020.

In one variation, three tendons are used to actuate each segment, including the steerable distal portion, although four or more tendons could be used. Three tendons can reliably articulate a segment in any direction without having to rotate the segment or endoscope about its longitudinal axis. The three cable tendons 3012 are preferably attached at the distal end of the segment 3020 close to the segment's edge, spaced equally apart. In FIG. 30B, tendons are attached at the two o'clock, six o'clock and 10 o'clock positions. It is desirable to use fewer tendons, because of space concerns, since the tendons controlling each segment project proximally to the actuators. Thus, two tendons could be used to control a segment. It may also be desirable to include one or more biasing element, e.g., a spring, to assist in articulating a segment in three dimensions. In another variation, two tendons may be used to articulate a segment in three dimensional space by controlling motion in two directions while rotating the segment about its longitudinal axis.

Figure 30D:
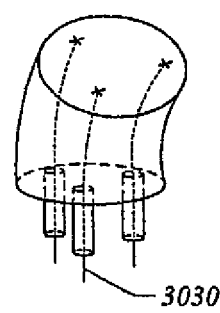
Figure 30E:
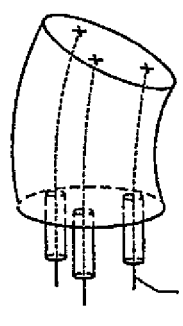
Figure 30F:
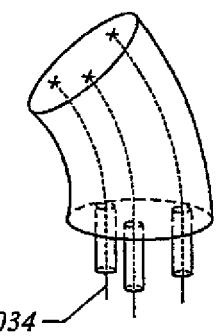

FIG. 30C shows a relaxed segment with three tendons attached. The tendon sleeves 3014 are shown attached to the proximal end of the segment 3022 directly below the corresponding cable attachment sites. FIGS. 30D, 30E and 30F show this segment bent by each of the controlling tendons 3010 separately.

As shown in FIG. 30D, applying tension by pulling on the first tendon 3030 results in a bending in the direction of the first tendon 3030. That is, looking down on the top of the unbent segment (as in FIG. 30A), if the first tendon is attached at the six o'clock position, then pulling on just this tendon results in bending the segment towards the six o'clock position. Likewise, in FIG. 30E, putting tension only on a second tendon 3032 attached at the two o'clock position results in bending the segment towards the two o'clock direction. Finally, pulling on the tendon in the ten o'clock position 3034 bends the segment towards the ten o'clock direction, as depicted in FIG. 30F. In all cases, the bending is continuous; the greater the tension applied, the further the bending (the α angle, in the x-z plane of FIG. 30A). A segment can be bent in any direction by pulling on individual tendons or a combination of two tendons. Thus, to bend the segment in the twelve o'clock direction, both the second 3032 and the third 3034 tendon could be pulled with equal force. Alternatively, first tendon 3030 in the six o'clock position may be pushed either alone or in combination with second 3032 and third tendons 3034 being pulled to result in the same configuration.

In all these variations, the circumferential locations of the tendons and/or biasing elements are illustrative and are not intended to be limited to the examples described herein. Rather, they may be varied according to the desired effects as understood by one of skill in the art.

Steerable endoscopes and colonoscopes may utilize a plurality of individual tensioning or control members, as described in greater detail in U.S. patent application Ser. No. 10/229,577 filed Aug. 27, 2002, which is incorporated herein by reference in its entirety. However, when a relatively large number of tensioning members are used to manipulate an endoscope for traversing a tortuous path, the organization and management for each of these tensioning members may be optimized according to embodiments of the methods and apparatus described herein.

Although the endoscope connectors and assemblies have been described for use with colonoscopes, the connector and engagement assemblies of the present invention may be configured for the efficient control of a wide variety of controllable articles in, the a number of other medical and industrial applications. In addition, they can also be configured for use with catheters, cannulas, surgical instruments, interluminal instruments, and/or introducer sheaths that use the principles described above for navigating through body channels or within the body. They may also be used for industrial applications such as inspection and exploratory applications within tortuous regions, e.g., machinery, pipes, difficult to access enclosures and the like.

In yet another variation, the motion controller assemblies can be used to control the automatically controlled proximal portion to follow the selected path and, if necessary, to return to a desired location using the three-dimensional model in the electronic memory of the controller. While the above illustrative embodiments have described mechanical connections and force transmissions of the first and second connector portions, it is to be appreciated that alternative embodiments of the connector of the present invention may be modified and adapted to accommodate other forms of energy, position, or force transfer including but not limited to, electrical, pneumatic, hydraulic and the like. Modification of the above-described assemblies and methods for carrying out the invention, and variations of aspects of the invention that are obvious to those of skill in the art are intended to be within the scope of the claims.

What is claimed is:

1. A medical system comprising:
a drive interface, a medical instrument, a first pair of complementary engagement features, and a second pair of complementary engagement features;
wherein the drive interface comprises a first drive element and a second drive element;
wherein the medical instrument comprises a force transmission interface removably engageable with the drive interface, and the force transmission interface comprises a first force transmission element and a second force transmission element;
wherein the first pair of complementary engagement features has an engaged state in which the first drive element is coupled to the first force transmission element and in which the first force transmission element is moveable in linear translation in a first direction in response to a drive force exerted by the first drive element;
wherein the second pair of complementary engagement features has an engaged state in which the second drive element is coupled to the second force transmission element and in which the second force transmission element is moveable in linear translation in the first direction in response to a drive force exerted by the second drive element; and
wherein the first pair of complementary engagement features is placed in the engaged state by relative movement of the first pair of complementary engagement features in a second direction perpendicular to the first direction, and the second pair of complementary engagement features is placed in the engaged state by relative movement of the second pair of complementary engagement features in the second direction.

2. The medical system of claim 1, wherein:
the first pair of complementary engagement features comprises a first force transmission element engagement feature coupled to the first force transmission element; and
the second pair of complementary engagement features comprises a second force transmission element engagement feature coupled to the second force transmission element.

3. The medical system of claim 2, wherein:
the first pair of complementary engagement features comprises a first drive element engagement feature coupled to the first drive element and configured to engage the first force transmission element engagement feature; and
the second pair of complementary engagement features comprises a second drive element engagement feature coupled to the second drive element and configured to engage the second force transmission element engagement feature.

4. The medical system of claim 3, wherein:
the first force transmission element engagement feature comprises a first protrusion; and
the second force transmission element engagement feature comprises a second protrusion.

5. The medical system of claim 4, wherein:
the first drive element engagement feature comprises a first recess configured to receive the first protrusion; and
the second drive element engagement feature comprises a second recess configured to receive the second protrusion.

6. The medical system of claim 4, wherein:
each of the first protrusion and the second protrusion comprises a tapered outer surface profile.

7. The medical system of claim 4, wherein:
each of the first protrusion and the second protrusion comprises a circular outer surface profile.

8. The medical system of claim 1, wherein:
rotation of the first drive element about a first axis of rotation exerts the drive force on the first force transmission element to move the first force transmission element in linear translation in the first direction; and
rotation of the second drive element about a second axis of rotation exerts the drive force on the second force transmission element to move the second force transmission element in linear translation in the first direction.

9. The medical system of claim 1, wherein:
the first drive element is movable in translation, and translation of the first drive element along the first direction exerts the drive force on the first force transmission element to move the first force transmission element in linear translation in the first direction; and
the second drive element is movable in translation, and translation of the second drive element along the first direction exerts the drive force on the second force transmission element to move the second force transmission element in linear translation in the first direction.

10. The medical system of claim 9, wherein:
the first drive element is actuatable in translation in the first direction; and
the second drive element is actuatable in translation in the first direction.

11. The medical system of claim 1, wherein:
the medical system comprises a first articulatable segment and a second articulatable segment;
the first force transmission element is coupled to the first articulatable segment to articulate the first articulatable segment; and
the second force transmission element is coupled to the second articulatable segment to articulate the second articulatable segment.

12. The medical system of claim 1, wherein:
the medical system further comprises a first motor and a second motor;
the first motor is operably coupled to the first drive element to actuate the first drive element; and
the second motor is operably coupled to the second drive element to actuate the second drive element.

13. A medical system comprising:
a force generation system and a medical instrument removably engageable with the force generation system;
wherein the force generation system comprises:
a first actuator comprising a first actuator engagement feature, and
a second actuator comprising a second actuator engagement feature;
wherein the medical instrument comprises:
an articulatable component,
a first force transmission element coupled to the articulatable component and comprising a first force transmission element engagement feature, and
a second force transmission element coupled to the articulatable component and comprising a second force transmission element engagement feature;
wherein the first force transmission element and the second force transmission element are linearly translatable and configured to actuate the articulatable component in response to linear translation of one or both of the first and second force transmission elements;
wherein the first actuator engagement feature is removably engageable with the first force transmission element engagement feature, and the second actuator engagement feature is removably engageable with the second force transmission element engagement feature;
wherein the first actuator engagement feature is configured to be placed in an engaged state with the first force transmission element engagement feature by movement along a first direction, and the second actuator engagement feature is configured to be placed in an engaged state with the second force transmission element engagement feature by movement along the first direction;
wherein in the engaged state of the first actuator engagement feature with the first force transmission element engagement feature, the first actuator engagement feature and the first force transmission element engagement feature translate together along a second direction perpendicular to the first direction in response to actuation of the first actuator; and
wherein in the engaged state of the second actuator engagement feature with the second force transmission element engagement feature, the second force transmission element engagement feature and the second actuator engagement feature translate together along the second direction in response to actuation of the second actuator.

14. The medical system of claim 13, wherein:
each of the first force transmission element engagement feature and the second force transmission element engagement feature comprises a tapered outer surface profile.

15. The medical system of claim 13, wherein:
the first actuator engagement feature comprises a first recess configured to receive the first force transmission element engagement feature; and
the second actuator engagement feature comprises a second recess configured to receive the second force transmission element engagement feature.

16. The medical system of claim 13, wherein:
the force generation system comprises a third actuator comprising a third actuator engagement feature; and
the medical instrument comprises a third force transmission element coupled to the articulatable component and comprising a third force transmission element engagement feature.

17. The medical system of claim 16, wherein:
the third force transmission element is linearly translatable and configured to actuate the articulatable component in response to linear translation of the third force transmission element.

18. The medical system of claim 16, wherein:
the third actuator engagement feature is removably engageable with the third force transmission element engagement feature.

19. The medical system of claim 16, wherein:
the third actuator engagement feature is configured to be placed in an engaged state with the third force transmission element engagement feature by movement along the first direction.

20. The medical system of claim 19, wherein:
in the engaged state of the third actuator engagement feature with the third force transmission element engagement feature, the third force transmission element engagement feature and the third actuator engagement feature translate together along the second direction in response to actuation of the third actuator.

* * * * *